(12) United States Patent
Cross et al.

(10) Patent No.: US 9,616,116 B2
(45) Date of Patent: Apr. 11, 2017

(54) DETOXIFIED ENDOTOXIN IMMUNOGENIC COMPOSITIONS AND USES THEREOF

(71) Applicants: Alan S. Cross, Chevy Chase, MD (US); Apurba K. Bhattacharjee, Kensington, MD (US); Wendell D. Zollinger, Leahi, UT (US); Steven M. Opal, Barrington, RI (US)

(72) Inventors: Alan S. Cross, Chevy Chase, MD (US); Apurba K. Bhattacharjee, Kensington, MD (US); Wendell D. Zollinger, Leahi, UT (US); Steven M. Opal, Barrington, RI (US)

(73) Assignees: UNIVERSITY OF MARYLAND, BALTIMORE, Baltimore, MD (US); THE MEMORIAL HOSPITAL OF RHODE ISLAND, Pawtucket, RI (US); UNITED STATES ARMY, Fort Detrick, MD (US)

( * ) Notice: Subject to any disclaimer, the term of this patent is extended or adjusted under 35 U.S.C. 154(b) by 0 days.

(21) Appl. No.: 14/636,951

(22) Filed: Mar. 3, 2015

(65) Prior Publication Data
US 2015/0174228 A1 Jun. 25, 2015

Related U.S. Application Data

(63) Continuation-in-part of application No. 12/083,993, filed as application No. PCT/US2006/041477 on Oct. 24, 2006, now abandoned.

(60) Provisional application No. 60/729,570, filed on Oct. 24, 2005.

(51) Int. Cl.
*A61K 39/095* (2006.01)
*A61K 39/108* (2006.01)
*A61K 39/00* (2006.01)

(52) U.S. Cl.
CPC ........ *A61K 39/0258* (2013.01); *A61K 39/095* (2013.01); *A61K 2039/55561* (2013.01); *A61K 2039/55583* (2013.01); *A61K 2039/58* (2013.01); *A61K 2039/70* (2013.01)

(58) Field of Classification Search
None
See application file for complete search history.

(56) References Cited

U.S. PATENT DOCUMENTS 6,902,743 B1 * 6/2005 Setterstrom et al. ......... 424/489
7,018,636 B1 * 3/2006 Bhattacharjee et al. . 424/197.11

OTHER PUBLICATIONS

Van der Ley et al. In: Final programme and abstracts of the 16th International Pathogenic Neisseria Conference, p. 35, #019, 2008.*
Bhattacharjee et al. J. Infect. Dis. 173: 1157-1163, 1996.*
Opal et al. J. Infect. Dis. 192: 2074-2080, ePub Nov. 10, 2005.*
Chen et al. In: Abstracts of the 44th Interscience Conference on Antimicrobial Agents and Chemotherapy, vol. 44, p. 255, #G-541, Oct. 30-Nov. 2, Washington D.C., 2004.*
Kandimalla et al. In: Toll and Toll-like Receptors: An Immunologic Perspective. (Ed) Tina Rich. Kluwer Academic Publishers, pp. 181-212, Jan. 2005.*
Cooper et al. J. Clin. Immunol. 24: 693-701, 2004.*
Halperin et al. Vaccine 21: 2461-2467, 2003.*
Cooper et al. Vaccine 22: 3136-3143, Mar. 2004.*
Sagara et al. Vaccine 27: 7292-7298, 2009.*
Klinman DM. Nature Reviews Immunology 4, 249-259, 2004.*
Davis et al. CpG ODN is safe and highly effective in humans as an adjuvant to HBV vaccine: Preliminary results of Phase I trial with CpG ODN 7909. Paper presented at: The Third Annual Conference on Vaccine Research, S25: 47, 2000.*
McCluskie et al. In: Immunopotentiators in Modern Vaccines. (Ed) Virgil E. Schijns. Academic Press, Chapter 5, pp. 73-92, 2006.*
Cross et al. Vaccine 21: 4576-4587, 2003.*

* cited by examiner

*Primary Examiner* — S. Devi
(74) *Attorney, Agent, or Firm* — Benjamin Aaron Adler

(57) ABSTRACT

The present invention provides an immunogenic composition of a lipopolysaccharide vaccine and a non-alum adjuvant. The immunogenic composition may be detoxified J5 core lipopolysaccharide of *Escherichia coli* non-covalently complexed with group B meningococcal outermembrane protein. Also provided are methods for preventing an infection caused by a Gram-negative bacteria in an individual via administering the immunogenic compositions to the individual.

5 Claims, 17 Drawing Sheets

DETOXIFIED ENDOTOXIN IMMUNOGENIC COMPOSITIONS AND USES THEREOF

CROSS REFERENCE TO RELATED APPLICATION

This application is a continuation-in-part patent application of application U.S. Ser. No. 12/083,993, filed Apr. 24, 2009, now abandoned, which is a U.S. national stage application under 35 U.S.C. §371 of international application PCT/US2006/41477, filed Oct. 24, 2006, now abandoned, which claims benefit of priority under 35 U.S.C. §119(e) of provisional application U.S. Ser. No. 60/729,570, filed Oct. 24, 2005.

STATEMENT OF FEDERALLY SPONSORED RESEARCH

This invention was made with government support under Grant Numbers AI042181, AI057168 and AI057159 awarded by the National Institutes of Health. The government has certain rights in the invention.

BACKGROUND OF THE INVENTION

Field of the Invention

The present invention relates generally to the field of immunology and vaccine development. More specifically, the present invention provides an immunogenic composition, comprising a lipopolysaccharide vaccine and a Toll-like receptor 9 (TLR9) agonist and its use in the prevention and treatment of sepsis and infection with biodefense agents.

Description of the Related Art

Gram-negative bacteria are causative agents of many life-threatening ailments which include pneumonia, plague, tularemia, meliodosis and sepsis. These bacteria can also be used as biowarfare agents. Gram-negative bacterial sepsis is a serious complication in patients residing in intensive care units (ICUs), undergoing abdominal surgery or incurring trauma or burns and in patients that develop prolonged neutropenia. Although antibiotic therapy plays an important role in limiting the incidence of this complication, there has been little change in the mortality of this condition once it develops as seen in the last few decades. Consequently, there has been considerable effort to devise new therapies to complement the advances in supportive care and anti-microbial therapy. An example of such therapy that is being explored is the use of vaccines.

Active or passive immunization with Gram negative bacterial endotoxin (or lipopolysaccharide, LPS) protects against lethal infection upon subsequent exposure to the same serotype of the organism from which the lipopolysaccharide was derived (known as "homologous protection"). However, such a vaccine does not protect against Gram-negative bacteria from other serotypes of that same species of bacteria or from different Gram-negative bacterial species (i.e. "heterologous" bacteria). This is because the antibody thus elicited is directed against the outermost sugars of the lipopolysaccharide molecule, each of which is specific for that one serotype.

In contrast, the core portion of the lipopolysaccharide, also called "core glycolipid", is widely conserved among many different Gram-negative bacteria such that antibodies directed against this core glycolipid provide heterologous protection i.e. protect against subsequent challenge with a wide spectrum of clinically relevant Gram-negative bacterial pathogens (1-2). Antibodies against an even more widely conserved region of the lipopolysaccharide molecule, the lipid A, have not been shown to be protective in either experimental or clinical studies of sepsis.

The ability of one such vaccine comprising lipopolysaccharide of an Rc chemotype mutant of *E. coli* 0111:B4 (*E. coli* J5) to provide protection against an array of Gram negative bacteria was examined in a previous study. The preparation of such a vaccine involved detoxification of the lipopolysaccharide first by alkaline treatment to cleave ester-linked fatty acids of the lipid A component of lipopolysaccharide followed by non-covalent complexing with the outer membrane protein (OMP) of *Neisseria meningitidis* Group B. This dLPS-J5/OMP vaccine protected against lethal gram-negative bacterial sepsis when administered either actively as a vaccine preventive strategy or passively as immune plasma in a neutropenic rat model of *Pseudomonas* sepsis (2-4). This vaccine was also used in the phase I clinical study in human subjects where these subjects were actively immunized with the vaccine (1).

Although the dLPS-J5/OMP vaccine demonstrated greater than 20 fold IgG antibody response to the core glycolipid structure of lipopolysaccharide in rabbits, mice and rats, human volunteers developed only a 2-3 fold increase above baseline antibody titers (1). The antibody response was polyclonal with generation of both IgM and IgG antibodies that persisted for at least 12 months (4).

Furthermore, previous passive protection studies had indicated that protection against lethal sepsis was dependent on the concentration of the antibody passively administered. It is also known that an immunogenicity to an antigen can be enhanced by administering the antigen in combination with an adjuvant. Examples of commonly used adjuvants in vaccine preparations include aluminium potassium sulfate, Freund's incomplete adjuvant, Freund's complete adjuvant, alum, synthetic polyribonucleotides and bacterial lipopolysacharides.

Bacterial DNA and synthetic oligodeoxynucleotides (ODN) that contain immunostimulatory unmethylated CpG motifs (CpG ODN) are potent TLR9 agonists (5-6) and have been shown to be potent B cell activators and effective immunoadjuvants when combined with a wide variety of types of antigens, including peptide-based vaccines (7). The CpG motifs also promote a Th1 type immune response which may further promote a combined innate and adaptive immune response essential to resist microbial invasion and promote antibacterial defense mechanisms (8). Additionally, these synthetic oligodeoxynucleotides have potentially benefited patients with asthma, enhance innate host defenses against neoplasia (9-10), and improve human vaccine responses (11). Despite the efficacy of the CpG oligodeoxynucleotides to function as an immunoadjuvant, to date CpG oligodeoxynucleotides have been used as vaccine adjuvants with primarily protein, protein/polysaccharide conjugates and with DNA vaccines (7, 9-11).

Thus, prior art is deficient in a vaccine that elicits a high antibody titer to offer protection against a wide array of Gram negative bacteria as well as monoclonal antibodies to treat infection by such bacteria. The current invention fulfils this long standing need in the art.

SUMMARY OF THE INVENTION

In one embodiment of the present invention, there is provided an immunogenic composition comprising a lipopolysaccharide vaccine and a non-alum adjuvant.

In a related embodiment of the present invention, there is provided a method of preventing an infection caused by Gram-negative bacteria in an individual. This method comprises administering an immunologically effective amount of the immunogenic composition described supra to the individual.

In another embodiment of the present invention, there is provided an method of preventing an infection caused by Gram-negative bacteria in an individual. This method comprises administering to the individual an immunogenic composition comprising a detoxified J5 core lipopolysaccharide of *E. coli* non-covalently complexed with group B meningococcal outermembrane protein at a concentration of about 5 µg to about 50 µg and a CpG 7909 oligodeoxynucleotide at a concentration of about 250 µg to about 500 µg.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 3A shows the binding of the antibody to whole bacterial cells. FIG. 3B shows the binding of the antibody to the biodefense LPS.

FIG. 4A shows the data of the ex vivo assay on whole blood. FIG. 4B shows the serum IgG levels. FIG. 4C shows the BAL IgG levels. FIG. 4D shows the serum IgA levels. FIG. 4E shows the BAL IgA levels.

FIG. 13A compares bacteremia in control, mice immunized with J5 and those immunized with J5+CpG. FIGS. 13B and 13C show bacterial count in liver and lung, respectively. FIG. 13D shows that immunized mice had fewer PMNs recruited to the lungs. FIG. 13E shows bacterial counts in the lung during the early time points.

DETAILED DESCRIPTION OF THE INVENTION

I. Definitions

Figure 1:
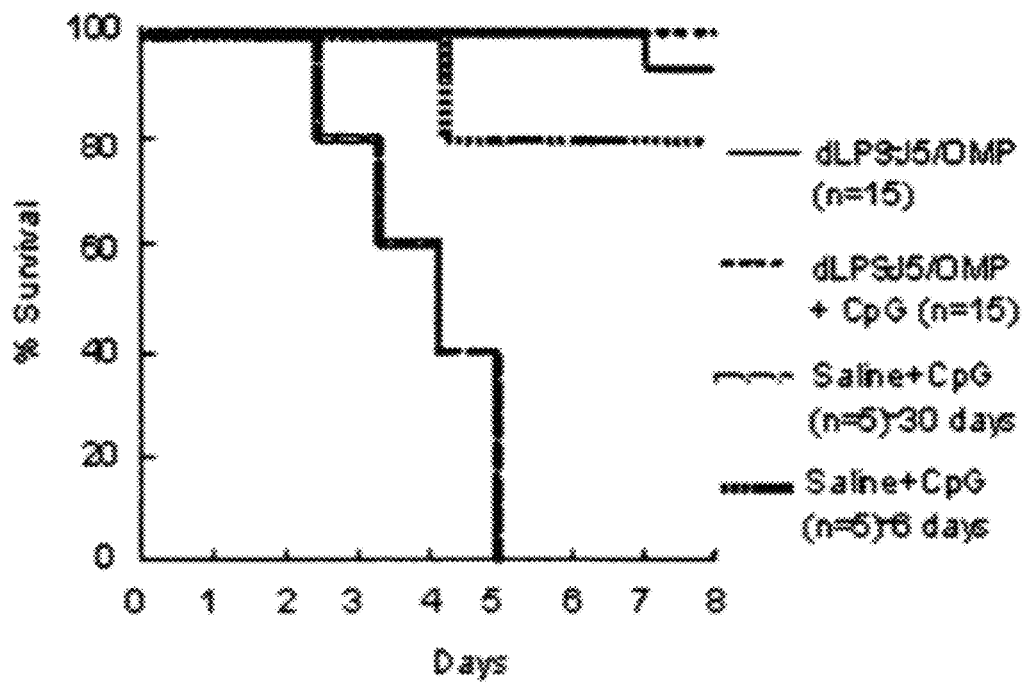
FIG. 1 shows the Kaplan-Meier survival plot of actively immunized BALB/c mice with the dLPS-J5/OMP vaccine; dLPS-J5/OMP vaccine+CpG oligodeoxynucleotides; CpG oligodeoxynucleotides+saline control group (day −6); and CpG oligodeoxynucleotides+saline control group (day −30). Both vaccine groups had a significantly greater survival rate than the CpG oligonucleotides+saline (day −30) control group ($P<0.01$ for both vaccine groups vs. control).

The use of the word "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

The use of the term "or" in the claims is used to mean "and/or" unless explicitly indicated to refer to alternatives only or the alternatives are mutually exclusive, although the disclosure supports a definition that refers to only alternatives and "and/or."

As used herein, the term "immunologically effective amount" refers to an amount that results in an improvement or remediation of the symptoms of the disease or condition due to induction of an immune response. Those of skill in the art understand that the effective amount may improve the patient's or subject's condition, but may not be a complete cure of the disease and/or condition.

As used herein, "active immunization" is defined as the administration of a vaccine to stimulate the host immune system to develop immunity against a specific pathogen or toxin.

As used herein, "passive immunization" is defined as the administration of antibodies to a host to provide immunity against a specific pathogen or toxin.

As used herein, "CpG oligonucleotides" are defined by the presence of an unmethylated CG dinucleotide in a CpG motif.

As used herein, "adjuvant" is defined as a substance which when included in a vaccine formulation non-specifically enhances the immune response to an antigen.

II. Present Invention

The present invention is directed to an immunogenic composition, comprising a lipopolysaccharide vaccine non-alum adjuvant. Generally, the non-alum adjuvant non-alum adjuvant is a Toll-like receptor 9 (TLR9) agonist, ADVAX, or HILTONOL.
Generally, the lipopolysaccharide vaccine may comprise a detoxified core lipopolysaccharide of a Gram-negative bacteria non-covalently complexed with group B meningococcal outer membrane protein (OMP). Representative examples of the core lipopolysaccharide in such a vaccine is not limited to but may include a J5 core lipopolysaccharide or any $R_a$-$R_e$ chemotype and a Gram-negative bacteria whose core lipopolysaccharide that can be used in the vaccines is not limited to but may include *Klebsiella, Pseudomonas, Burkholderia, Francisella, Yersinia, Enterobacter, Escherichia coli, Serratia, Actinobacter, Salmonella,* or *Shigella*. The TLR9 agonist may be a synthetic oligodeoxynucleotide comprising one or more immunostimulatory unmethylated CpG motifs. Representative examples of such oligodeoxynucleotides that can be used as an immunoadjuvant in this immunogenic composition is not limited to but may include a CpG 7909 oligodeoxynucleotide, or any other immunostimulatory CpG oligodeoxynucleotide.

The present invention is also directed to a method of preventing an infection caused by Gram-negative bacteria in an individual, comprising: administering an immunologically effective amount of the immunogenic composition described supra. Generally, such a composition may enhance an antibody response, reduce the levels of inflammatory cytokines and the levels of endotoxins and decrease the bacterial load in the individual to prevent the infection caused by the Gram-negative bacteria in the individual. Examples of Gram-negative bacteria causing the infection is not limited to but may include *Klebsiella, Pseudomonas, Burkholderia, Francisella, Yersinia, Enterobacter, Escherichia coli, Serratia, Actinobacter, Salmonella,* or *Shigella*. Generally, an individual benefitting from such a method may be one who is healthy, has incurred trauma, will or has undergone surgical procedure, is at high risk of developing occupation-related or heat related injuries or is at a risk of developing graft versus host disease subsequent to bone marrow or stem cell transplantation. Furthermore, the concentration of the vaccine in the immunogenic composition may be about 5 µg to about 50 µg and the concentration of the TLR9 agonist in the immunogenic composition may be about 250 µg to about 500 µg. Additionally, the immunogenic composition may be administered subcutaneously, intramuscularly, intranasally or mucosally.

The present invention is also directed to a method of preventing an infection caused by a Gram-negative bacteria in an individual, comprising: administering to the individual an immunogenic composition comprising a detoxified J5 core lipopolysaccharide of *E. coli* non-covalently complexed with group B meningococcal outer membrane protein at a concentration of about 5 µg to about 50 µg and a CpG 7909 oligodeoxynucleotide at a concentration of about 250 µg to about 500 µg. Generally, the composition may enhance antibody response, reduce the levels of inflammatory cytokines and the levels of endotoxins and decrease bacterial load in the individual to prevent the infection caused by the Gram-negative bacteria in the individual. All other aspects regarding examples of Gram-negative bacteria causing the infection, individuals that will benefit from this method and routes of administering the composition discussed supra.

The present invention discloses a novel vaccine adjuvant composition comprising detoxified Gram negative J5 core lipopolysaccharide/group B meningococcal outer membrane protein complex (dLPS-J5/OMP) as the vaccine and a Toll-like receptor 9 (TLR9) agonist as the adjuvant. The present invention further discloses the use of a CpG oligodeoxynucleotide that is a synthetic oligodeoxynucleotide comprising immunostimulatory unmethylated CpG motifs as the adjuvant. More specifically, a representative CpG oligodeoxynucleotide that can be used as an immunoadjuvant is CpG 7909 oligodeoxynucleotide. The TLR9 agonist or CpG oligonucleotide may be adminstered separated or conjugated together chemically as is known in the art. Furthermore, the present invention is drawn to the use of the immunogenic composition comprising dLPS-J5/OMP and CpG 7909 for the prevention and treatment of sepsis and infection with biodefense agents. In addition to the utility of the vaccine in preventing and treating sepsis, the present invention also contemplates its use in the prevention of infections caused by select agents.

Although there was a great interest in the use of anti-endotoxin antibodies in the 1970s and 1980s, clinical studies with monoclonal antibodies to lipid A were not successful. As a result, effort was focused on developing cytokine inhibitors and other inhibitors of inflammatory mediators. However, during the same time a killed, whole bacterial cell vaccine was made from *E. coli* J5 mutant and used for immunization of healthy volunteers. Sera from these immunizations when used in a clinical trial demonstrated that the post-immunization sera was highly protective in patients with Gram-negative bacterial sepsis. But this vaccine was never developed into a refined vaccine. Additionally, there are many experimental vaccines for sepsis that are being developed, but none of these have progressed to clinical trials. In fact, one such vaccine that requires incorporation of multiple lipopolysaccharide species into liposomes has not been used in clinical trials because of the difficulty in making it on commercially. Furthermore, although CpG oligodeoxynucleotides have been used as immunoadjuvant for some protein vaccines such as hepatitis B (11-12) and influenza A (12) but never with a lipopolysaccharide. CpG oligodeoxynucleotide might also be used to stimulate polysaccharide antibody responses in *Haemophilus influenzae* type B conjugate vaccine (13) and the pneumococcal vaccine (14).

In distinct contrast, the vaccine disclosed by the present invention does not require complex preparation and discloses the ability of non-alum adjuvants such as CpG oligodeoxynucleotides to enhance antibody response to lipopolysaccharide based vaccine. Mice were immunized with the dLPS-J5/OMP vaccine with or without the adjuvant. The vaccine-induced antibody response was examined in a cecal ligation and puncture model (CLP). This model generates a bacteremic infection by endogenous enteric bacteria and therefore, serves as clinically relevant test system. The mechanism of protection offered by the vaccine was further investigated in this experimental model.

Immunization with the dLPS-J5/OMP vaccine without the adjuvant resulted in >20 fold increase in anti-core lipopolysaccharide antibody levels which was further increased 5 fold on addition of CpG oligodeoxynucleotide to the vaccine. The vaccine adjuvant combination was highly protective not only in the neutropenic rat model of sepsis but also in a model of polymicrobial sepsis, the CLP model in mice. In the CLP model, the vaccine adjuvant combination did not show a superior protection over vaccine alone since the protection with the vaccine alone was nearly 100%. However, evaluation of surrogate markers for vaccine effectiveness (cytokine, endotoxin level, bacterial loads) suggested that the vaccine adjuvant combination might be superior in a more severe model of sepsis.

For instance, circulating endotoxin levels and the quantity of gram-negative bacteria in organ cultures were significantly reduced by the vaccine administration. These results are compatible with the hypothesis that anti-core glycolipid antibodies bind to microbial antigens and are being cleared in vivo at a greater rate than other circulating immunoglobulins in animals with polymicrobial gram-negative sepsis. There was also a decrease in local inflammatory cytokine production within the peritoneum in immunized mice when compared to control animals. Lipopolysaccharide levels in the peritoneum were diminished albeit not significantly following active immunization with the vaccine. Anti-core glycolipid antibody levels were specifically depleted following CLP than total circulating IgG levels or IgG levels to the OMP part of the vaccine complex. This lack of comparable reductions in circulating immunoglobulin to OMP antigen argues against a generalized, non-specific decrease in antibody levels from increased catabolism, altered tissue distribution or decreased synthesis of immunoglobulins. These results in the CLP model support findings with vaccine protection in the neutropenic rat model of sepsis with either *Pseudomonas aeruginosa* or *Klebsiella pneumoniae* (2, 4).

Thus, the results obtained in the CLP model demonstrated that the detoxified LPS-J5/OMP vaccine induced high titer antibodies against the core glycolipid of lipopolysaccharide and functioned in vivo to promote clearance of gram-negative bacteria and improve the outcome in experimental, polymicrobial intra-abdominal sepsis. The results also showed that the efficacy of the vaccine could be improved when combined with CpG oligodeoxynucleotide.

Additionally, it was reported that boiled, whole bacterial vaccine prepared from *E. coli* J5 (Rc chemotype) 0111:B4 elicited antibody in rabbits protected neutropenic rats from lethal gram-negative infection (15). Since affinity purified IgG prepared from this antisera was protective, a vaccine with detoxified lipopolysaccharide from *E. coli* 0111:B4 (Rc chemotype mutant) was also developed (1). The detoxified *E. coli* J5 lipopolysaccharide was non-covalently complexed to group B meningococcal OMP to maintain a critical conformational epitope present in the native core glycolipid structure of lipopolysaccharide (2). This vaccine, like the heat-killed bacterial vaccine, was protective in both active and passive models in the neutropenic rat model (4). This protection was associated with both decreased levels of circulating cytokines, bacterial endotoxin and reduced concentrations of bacteria in target organs.

Based on the success in the use of this vaccine in the animal model, the vaccine was used in phase I clinical testing in normal human volunteers (16). The dLPS-J5 OMP vaccine was given in doses from 5-25 mcg (based upon its lipopolysaccharide content) to 24 volunteers in a three dose schedule from day 0 to day 28 and day 56. The vaccine was well tolerated with no significant systemic toxicity and no abnormal laboratory values attributed to the vaccine itself (1, 15). Approximately two-thirds of these subjects experienced some mild to moderate pain at the injection site which usually resolved within 28-48 hours. Whereas preclinical studies in other mammals consistently demonstrated greater than 20 fold increases in antibody concentration, human volunteers had only a 3 fold increase over pre-immune baseline levels. Despite the rather modest increase in antibody levels, immune plasma from volunteers reduced cytokine generation in a whole blood assay (15). Since studies in the neutropenic rat model indicated the need for high levels of anti-core glycolipid antibody to offer protection (3), an effort was undertaken to determine if immunoadjuvants would increase vaccine-induced antibody response.

The present invention demonstrated that addition of CpG oligodeoxynucleotides to the detoxified lipopolysaccharide vaccine resulted in a marked increase in anti-J5 LPS antibody responses (Table 1). For example, there was a 5 fold increase in the antibody concentration of IgG antibodies with the addition of CpG oligodeoxynucleotides to the vaccine. Each animal that received CpG oligodeoxynucleotides along with the vaccine had higher IgG levels than any animal in receipt of vaccine alone. While alum and CpG oligodeoxynucleotides have been used together and shown to have synergy in various preclinical vaccines, as well as for a hepatitis B vaccine in clinical testing (11, 17-18) the addition of alum to this vaccine significantly reduced antibody responses to this vaccine (Table 1). This reduction in the antibody response could be due to blocking of the alignment and/or exposure of a critical conformational epitope in this vaccine that is normally recognized by the host immune system by alum when administered with CpG ODN.

TABLE 1

Immunization of mice (CLP model) with dLPS-
J5/OMP vaccine with and without adjuvants

| Treatment | IgG Level (ng/ml) (range) | SEM |
|---|---|---|
| Vaccine[a] | 11,259 (3,036-23,880) | 3,253 |
| Vaccine + CpG | 72,052* (26,333-219,650) | 29,889 |
| Vaccine + Alum | 25,472 (5,522-54,355) | 9,306 |
| Vaccine + CpG + Alum | 6,197** (4,380-8,976) | 828 |
| CpG + Alum | 85 (51-151) | 15 |
| Control | 60 (0-87) | 13 |

[a]Vaccine refers to dLPS-J5/OMP vaccine; Mice (6/group) were immunized with vaccine (10 g, based on LPS content), CpG (25 g/mouse) or alum (10 g) as indicated at time 0, and days 14 and 28. Sera was obtained at day 35 and sera from individual mice were examined in an anti-J5 LPS ELISA.s);
*vaccine alone vs. vaccine + CpG-P < .01;
**vaccine + CpG + alum vs. vaccine + CpG P < .01

The adjuvant effect of CpG oligodeoxynulceotides was also evident in animals that underwent active immunization prior to the CLP procedure. Comparable with previous experiments, a prominent increase in the geometric mean concentration of anti-J5 dLPS IgG levels was attained after receiving a three dose series of immunizations and this provided a high level of protection. Since the protection observed with J5 vaccine alone was >90%, it was difficult to show a survival advantage when the vaccine was given with CpG.

Additionally, the administration of a single dose of CpG given 6 days prior to CLP offered protection in mice from lethal sepsis as previously reported (8). This protection had been attributed to enhanced phagocytic function and immune clearance induced by CpGs. However, the administration of CpG oligodeoxynucleotide alone with the 3 dose vaccine schedule 30 days before CLP provided no survival benefit. The CpG oligodeoxynucleotide in the present invention appeared to function as an adjuvant for the vaccine with enhancement of adaptive immune responses and not as an independent non-specific stimulant of innate host defenses (18-19).

Furthermore, the superior protective effect of the addition of CpG oligodeoxynucleotides in the CLP model compared with dLPS-J5/OMP vaccine alone could not be demonstrated (FIG. 1). This may be due to the fact that the antibody response induced by the vaccine alone, even with its partial depletion during sepsis, produced antibody levels far in excess (mean core glycolipid antibody concentration-151 microgram/ml) of that required for protection. Both vaccine alone and vaccine plus CpG oligodeoxynucleotide groups had lower levels of local cytokines within the peritoneum and lower levels of bacteria found within organs following CLP. Despite both vaccine alone and vaccine+CpG oligodeoxynucleotide having high levels of anti-core glycolipid antibody, the lowest TNF concentration and lipopolysaccharide concentration was found in the vaccine group that received the CpG oligodeoxynucleotide immunoadjuvant. This suggested that with a higher level of sepsis severity, the addition of CpG oligodeoxynucleotide to the vaccine may provide better protection, especially in more severe models of severe sepsis and septic shock.

Furthermore, it was observed that the antibodies that were induced by the vaccine were capable of recognizing Burkholderia pseudomallei and Francisella tularensis. In case of Burkholderia, vaccine antibodies decreased the ability of the Burkholderia lipopolysaccharide to generate cytokines in human peripheral blood mononuclear cells. Hence, the functional activity of these antibodies are also demonstrated against tularemia and Y. pestis, the agent of plague. Additionally, the protective ability of the vaccine with and without the CpG adjuvant was examined in a model of Gram-negative bacterial pneumonia when administered parenterally and intranasally. The vaccine with the CpG adjuvant was observed to be highly protective when the mice were challenged with Klebsiella after active immunization. Hence, the efficacy of the vaccine-adjuvant combination is also be demonstrated by challenging with Pseudomonas and other select agents. Further, the efficacy and the mechanism of action of the vaccine with and without the CpG adjuvant such as CpG 7909 is also examined in Phase I trial with human subjects. Since it appeared that the antibody facilitated the uptake and killing of bacteria by macrophages in vitro and promoted clearance of the bacteria and/or lipopolysaccharide from the circulation, the macrophage uptake assay will be used for rapid screening of either lots of antibody or the production of monoclonal antibodies.

Despite the above-discussed results, the mechanism of protection afforded by this vaccine has not been fully elucidated. Since there was a decreased bacterial load of aerobic organisms in the organs of immunized mice, one mechanism of protection of the vaccine may be the uptake and killing of bacteria by tissue phagocytes. Previous studies involving passive administration of anti-core glycolipid antibodies had shown that post-immunization sera promoted the clearance of both lipopolysaccharide and bacteria from the circulation (4). Thus, the present invention contemplates investigating whether this was a primary mechanism of protection of the vaccine so that surrogate markers for vaccine efficacy can be developed for the human vaccine project. Further, based on the results described herein, it is also contemplated that the vaccine-induced antibodies might promote clearance of Bacteroides fragilis or other anaerobic, gram-negative, enteric microflora as well.

In the case of pneumococcal immunization or hepatitis B immunization (20-21), it had been shown that functional assays, and not simple binding assays correlated with vaccine-elicited protection. Unlike the situation with these microbial pathogens where only a single activity (opsonization or neutralization) appeared to be of primary importance, the host response to bacterial lipopolysaccharide was considerably more complicated. There were a wide range of potential, clinically relevant activities initiated by this microbial mediator and it was difficult to predict which function was the most appropriate target for inhibition by antibody-induced by the vaccine. Hence, the effect of vaccine-induced antibody on lipopolysaccharide-induced activities will be systematically analyzed to identify assays that would correlate with vaccine-elicited protection.

Nevertheless, based on these results, the present invention contemplates using the vaccine to raise antibodies for passive protection of individuals with sepsis. Thus, patients suspected of sepsis could receive the antibodies in conjunction with standard therapy, e.g. antibiotics and supportive care. Additionally, as observed with experimental vaccines for Klebsiella and Pseudomonas, active immunization of patients upon arrival to the Shock and Trauma center induced antibodies in the patients and healthy individuals, the present invention contemplates using this vaccine in the same manner to prevent development of sepsis during the hospitalization of such individuals. Thus, this vaccine could be administered to patients who will undergo elective abdominal, urologic or gynecologic surgery that have a high risk of sepsis. This vaccine could also be given to individuals who work in areas with a high risk of injury such as policeman, fireman, military, loggers.

Studies have shown protection with active and passive J5dLPS-OMP parenteral immunization against lethal heterologous monomicrobial and polymicrobial sepsis (2, 4, 22) which was dependent on anti-CGL IgG antibodies (3). The purpose of the present invention was 1) to assess whether the J5dLPS-OMP vaccine could elicit antibody responses in the respiratory tract by different routes of administration, 2) to determine if this CGL vaccine can protect against lethal heterologous GNB pneumonia, and 3) to identify a potential mechanism of action for antibodies elicited by the sepsis vaccine.

Only a few previous studies have examined the effect of i.n. immunization with glycolipid-based vaccines. Vaccines constructed from the detoxified LOS of nontypeable *Haemophilus influenzae* (23) and *Moraxella catarrhalis* (24) and non-detoxified LPS from *Brucella melitensis* (25-26) and *Shigella flexneri* 2a and *Shigella sonnei* (27) have shown enhanced clearance or protection from pneumonia with homologous bacterial species. A live attenuated *Salmonella* expressing the 0 antigen portion of LPS from *Pseudomonas aeruginosa* provided protection from heterologous strains of *P. aeruginosa* (28). The present invention shows protection from heterologous bacterial species.

The results presented herein are consistent with the finding that i.n. delivery of glycolipid-based vaccines elicits both systemic and mucosal IgG and IgA, but parenteral delivery did not elicit a robust local IgA response. While there was no gross blood in the BALF which might indicate that systemic IgG from serum might have leaked inadvertently into the BAL samples during the lung washes, the possibility cannot be completely ruled out. If IgG is sufficient for protection from GNB pneumonia, then parenteral vaccination may be adequate. However, if secretory IgA is an important line of defense against pathogens of the respiratory mucosal lining, then i.n. or alternative mucosal routes of administration might provide a more protective immune response.

Secretory IgA is generally accepted as helpful in the clearance of pathogens in the gut and nasal mucosa; this is done primarily by "immune exclusion" (29). However, secretory IgA does not fix complement nor induce phagocytosis in neutrophils or Kuppfer cells (30). No studies that definitively demonstrate that secretory IgA grants any protection in the lower respiratory tract are known so far. In fact, the protective antibody of the lower respiratory tract is believed to be serum IgG (29, 21). Furthermore, IgA deficiency is one of the most common primary immunoglobulin deficiencies yet most individuals are clinically asymptomatic. These data argue against a role for IgA as a protective factor in pneumonia.

Using the model of lethal heterologous GNB pneumonia, the present invention demonstrated a survival benefit with active i.n. immunization of J5dLPS-OMP with CpG compared to control animals, using an outbred strain of mice. The present invention also showed significant differences in severity of pneumonia, as assessed by weight loss, between i.n. vaccinated and control mice. *Klebsiella pneumonia* O1:K2 was used as the challenge organism because its high virulence (16). The ICR mice were challenged by IT route of administration with *Pseudomonas aeruginosa* isolates PA01 and PA12.4.4, doses in excess of $10^8$ CFU failed to achieve 50% lethality. Therefore, the in vivo vaccination protection studies were not performed with *Pseudomonas* because the animal model would more likely reflect a model of endotoxemia rather than pneumonia.

In the present invention, CpG was used as a potential immunostimulatory adjuvant for the J5dLPS-OMP vaccine. The specific dinucleotide motifs in these chemically synthesized sequences are known to stimulate antigen presenting cells via Toll-like receptor 9 and are optimized for each animal species. These CpG ODN have been shown to significantly enhance systemic and mucosal immune responses to protein vaccines, such as purified hepatitis B surface antigen, when given mucosally (32). On the other hand, CpG ODN can activate non-specific innate immune responses resulting in protection from lethal bacterial challenges, yet these systemic responses wane rapidly (33-35) and persist less than 10 days when administered via the respiratory tract (36-37). The improved survival from pneumonia in mice that received vaccine and CpG i.n. are not likely the result of non-specific responses from CpG since our mice were administered the last dose of CpG at least 2 weeks prior to challenge.

The present invention identified a correlation with decreased organ loads in protection from lethal challenge and enhanced killing of both *Klebsiella pneumoniae* and *Pseudomonas aeruginosa* with primary macrophages which seems to be based on the antibodies elicited by the vaccine. An alternative explanation for the modest but significantly enhanced in vitro bactericidal activity is the nonspecific, non-macrophage enhancement of antibacterial lung defenses (38). The increased colony counts with addition of L-NIL, which blocks nitric oxide production and is a critical antibacterial effector in phagocytes, confirms that macrophage-mediated killing was probably responsible for the differences in viable bacterial counts in our assay. Since protection from an infection can be achieved against a number of mucosal pathogens with the elicitation of high levels of serum IgG (39), the magnitude of BALF anti-CGL IgG elicited by parenteral administration of the CGL vaccine might obscure the contribution of local anti-CGL IgA antibodies produced by i.n. vaccination. The reduction in killing with the dilution of serum 1000-fold does not rule out the possibility of non-Ig, non-complement opsonins as the reason for enhanced in vitro killing.

Resident AM differ from other macrophages, such as PM, in that they are capable of ingesting large quantities of foreign particulate while remaining relatively quiescent and avoiding the potential for collateral tissue damage by the elaboration of pro-inflammatory responses in the lung (40). However despite those differences, the present invention shows that AM were similar to PM in their ability to kill opsonized PAO1 in vitro. In conclusion, the ability of this vaccine to protect against lethal heterologous GNB pneumonia either by mucosal IgA and/or systemic and mucosal IgG following intranasal or parenteral routes of administration warrants further investigation.

Figure 11:
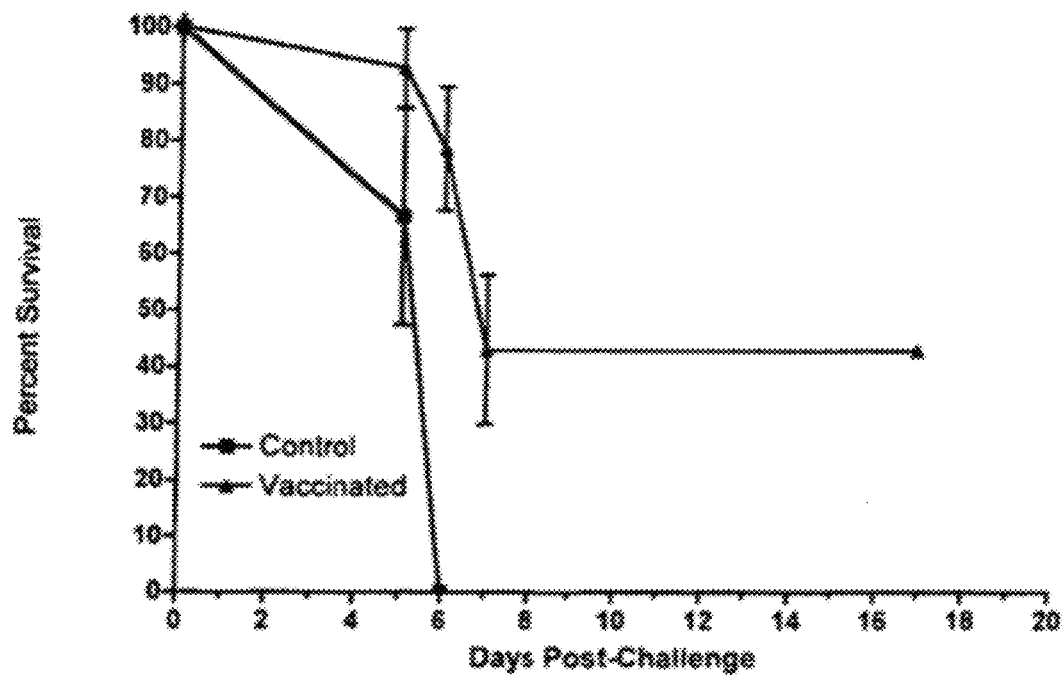
FIG. 11 shows the Kaplan-Meier survival curve for mice in a respiratory tularemia mouse model.

The present invention also examined the effect of the vaccine disclosed herein against biological threat agent such as the Gram-negative bacteria, *Francisella tularensis*, which is an agent of tularemia. In this study, the mice were immunized with the vaccine with and without the CpG adjuvant and the effect of the vaccine compared between vaccine-immunized mice and control mice. There was no difference between vaccine alone and vaccine+CpG and hence were grouped together as vaccinated (FIG. 11). In contrast, immunization with the vaccine protected the mice from lethal inhalational tularemia.

The present invention demonstrates that intranasal immunization with J5dLPS/OMP vaccine+CPG protected mice from lethal pulmonary infection with LVS and in initial experiments with the more virulent type A strain SchuS4. Given the decreased bacterial organ load, vaccine induced antibodies may have enhanced phagocyte killing of FT but this must be directly examined. Decreased tissue cytokines may reflect reduced bacterial load in immunized mice. Since the LPS of FT differs from that of other gram negative bacteria, the epitope on FT recognized by vaccine-induced antibodies is not clear. While CPG stimulates innate immune mechanisms, its effect usually wanes by 7 days, well before the i.t challenge and cannot explain the observed protection. The methods and compositions of the present invention would also be useful against other Gram negative bacteria such as *Yersinia pestis*, the agent of plague.

Furthermore, if the vaccine is found to be effective in preventing or ameliorating infection following exposure to some select agents, then it could also be used to counter bioterrorism. As discussed above, the vaccine without the CpG adjuvant has already been safely administered to humans in a phase I trial. However, there is a considerable evidence that endotoxin leakage from the gut to the circulation may play a role in heat-related injury and in graft-versus-host disease in stem cell transplantation. If this is true, then this vaccine can be given to prevent potentially lethal complications of these conditions.

The concentration of the lipopolysaccharide vaccine in the immunogenic composition may be from about 5 µg to about 50 µg. Specifically, the concentration may be about 5 µg-10 µg; 10 µg-15 µg; 15 µg-20 µg; 20 µg-25 µg; 25 µg-30 µg; 30 µg-35 µg; 35 µg-40 µg; 40 µg-45 µg and 45 µg-50 µg. The concentration of TLR9 agonist in the immunogenic composition is about 250 µg-500 µg. Specifically, the concentration may be about 250 µg-30 µg; 30 µg-350 µg; 350 µg-400 µg; 400 µg-450 µg and 450 µg-500 µg. The dose at which the antibody may be administered to the individual may be from about 100 mg/kg-1500 mg/kg. Specifically, the dose may be 100 mg/kg-200 mg/kg; 200 mg/kg-300 mg/kg; 300 mg/kg-400 mg/kg; 400 mg/kg-500 mg/kg; 500 mg/kg-600 mg/kg; 600 mg/kg-700 mg/kg; 700 mg/kg-800 mg/kg; 800 mg/kg-900 mg/kg; 900 mg/kg-1000 mg/kg and 1000 mg/kg-1500 mg/kg. Of course, all of these amounts are exemplary, and any amount in-between these points is also expected to be of use in the invention.

Treatment methods will involve preventing an infection in an individual with an immunologically effective amount of a composition containing lipopolysaccharide vaccine and a TLR9 agonist or an antibody generated using the immunogenic composition. An immunologically effective amount is described, generally, as that amount sufficient to detectably and repeatedly induce an immune response so as to prevent, ameliorate, reduce, minimize or limit the extent of a disease or its symptoms. More specifically, it is envisioned that the treatment with the immunogenic composition enhances antibody response, reduces the level of inflammatory cytokines and the levels of endotoxins and decreases the bacterial load in the individual to prevent the infection caused by the Gram-negative bacteria.

The immunologically effective amount of the immunogenic composition or antibody generated thereof to be used are those amounts effective to produce beneficial results, particularly with respect to preventing the infection caused by the Gram-negative bacteria, in the recipient animal or patient. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value.

The immunogenic composition disclosed herein and the antibody generated thereof may be administered either alone or in combination with another drug, a compound, or an antibiotic. Such a drug, compound or antibiotic may be administered concurrently or sequentially with the immunogenic composition or antibody disclosed herein. The effect of co-administration with the immunogenic composition or antibody is to lower the dosage of the drug, the compound or the antibiotic normally required that is known to have at least a minimal pharmacological or therapeutic effect against the disease that is being treated. Concomitantly, toxicity of the drug, the compound or the antibiotic to normal cells, tissues and organs is reduced without reducing, ameliorating, eliminating or otherwise interfering with any cytotoxic, cytostatic, apoptotic or other killing or inhibitory therapeutic effect of the drug, compound or antibiotic.

The composition described herein and the drug, compound, or antibiotic may be administered independently, either systemically or locally, by any method standard in the art, for example, subcutaneously, intravenously, parenterally, intraperitoneally, intradermally, intramuscularly, topically, enterally, rectally, nasally, buccally, vaginally or by inhalation spray, by drug pump or contained within transdermal patch or an implant. Dosage formulations of the composition described herein may comprise conventional non-toxic, physiologically or pharmaceutically acceptable carriers or vehicles suitable for the method of administration.

The immunogenic composition or antibody described herein and the drug, compound or antibiotic may be administered independently one or more times to achieve, maintain or improve upon a therapeutic effect. It is well within the skill of an artisan to determine dosage or whether a suitable dosage of either or both of the immunogenic composition or antibody and the drug, compound or antibiotic comprises a single administered dose or multiple administered doses.

As is well known in the art, a specific dose level of such an immunogenic composition or antibody generated thereof for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards.

One of skill in the art realizes that the immunologically effective amount of the immunogenic composition or the antibody generated thereof can be the amount that is required to achieve the desired result: enhance antibody response, reduce the level of inflammatory cytokines and levels of endotoxins, decrease the bacterial load, etc.

Administration of the immunogenic composition of the present invention and the antibody generated thereof to a patient or subject will follow general protocols for the administration of therapies used in treatment of bacterial infections taking into account the toxicity, if any, of the components in the immunogenic composition, the antibody and/or, in embodiments of combination therapy, the toxicity of the antibiotic. It is expected that the treatment cycles would be repeated as necessary. It also is contemplated that various standard therapies, as well as surgical intervention, may be applied in combination with the described therapy.

As is known to one of skill in the art the immunogenic composition described herein may be administered along with any of the known pharmacologically acceptable carriers. Additionally the immunogenic composition can be administered via any of the known routes of administration such as subcutaneous, intranasal or mucosal. Furthermore, the dosage of the composition to be administered can be determined by performing experiments as is known to one of skill in the art.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1

Vaccine Antigen and Vaccine Adjuvant

The rodent-specific CpG ODN (#1826) was procured from Coley Pharmaceutical Group (Wellesley, Mass.). The dLPS-J5/OMP vaccine was developed in a GMP facility (1). The meningococcal OMP was derived from lipopolysaccharide-free, membrane-free proteosomes and complexed with detoxified *E. coli* J5 LPS.

Example 2

Assays and Reagents

Murine cytokine and chemokine levels were measured using the BioPlex 16 multiplex cytokine assay (Bio-Rad, Hercules, Calif.). LPS levels were measured using a quantitative turbidimetric Limulus Amebocyte lysate assay, (Associates of Cape Cod Woods Hole, Mass.). All other reagents and chemicals were provided by Sigma (St. Louis, Mo.) unless otherwise stated.

Example 3

Cecal Ligation and Puncture Model

Pathogen-free albino, female BALB/c mice (Charles River Laboratories, Cambridge, Mass.) were used in the experiments. The animals were 8-12 weeks of age and were allowed to adapt to the laboratory for seven days before any experiments were initiated. The animals were allowed to eat and drink ad libitum.

The experimental design was modeled after previously published investigations (41). After an overnight fast, animals were anesthetized with parenteral administration of 200 microliter intraperitoneal injection of ketamine-9 mg/ml (Abbott, North Chicago, Ill.) and xylazine-1 mg/ml (Phoenix Pharmaceuticals, St. Josephs, Mo.). Under sterile conditions a midline abdominal incision was made and the cecum was identified and exteriorized. The cecum was then ligated with a 4-0 monofilament ligature and the antemesenteric side of the cecum was punctured twice with a 23 gauge needle. A scant amount of luminal contents was expressed through each puncture site to assure patency. The cecum was then returned to the abdomen and the fascia and skin was closed in two layers.

Lidocaine (1% without epinephrine) was applied to the surgical site along with topical antibiotic (bacitracin). A single I.M. dose of trovafloxacin (Pfizer, New York) (20 mg/kg) was administered along with 1.0 ml of normal saline subcutaneously. The animals were warmed externally until they were able to regain normal mobility. Mortality was monitored over seven days. Moribund animals that were unable to right themselves and were hypothermic ($<33°$ C. by digital infrared thermometry) were euthanized and considered lethally infected. Each animal underwent necropsy examination where liver and spleen tissues were removed for quantitative organ cultures on MacConkey media and *enterococcus*-specific media (BBL, Cockeysville, Md.). A 1 ml sample of peritoneal fluid was obtained following a lavage of the peritoneum with 5 ml of normal saline at the time of autopsy.

Example 4

Vaccine Schedule

The dJ5LPS/OMP vaccine was administered at 10 μg or 20 μg (based on dLPS content) intramuscularly at 0, 2 and 4 weeks. After a one month rest period, the CLP was performed. Blood samples were collected at baseline, one month after the final immunization and before CLP and then 48 hours after CLP. The CpG oligodeoxynucleotides immunoadjuvant (25 μg/mouse) was administered admixed with the vaccine in the same syringe. The control group received CpG oligodeoxynucleotides with saline at the same dose and time schedule. As an additional control, CpG oligodeoxynucleotides was administered to a separate set of animals (n=5) at 25 μg/animal 6 days prior to the CLP since previous study (8) had indicated that CpG alone may have significant immunoprophylactic effects when administered shortly before major systemic insults. Antibody levels to core glycolipid structures were measured using a standard ELISA method (1).

Example 5

Statistical Analyses

Numeric data was analyzed by a non-parametric Kruskal-Wallis one way analysis of variance with Dunn's multiple comparisons test for multiple groups of mice or Mann-Whitney U test for two groups of mice. A Kaplan-Meier survival plot was used to analyze outcome in each treatment group and differences in survival time were measured by the log-rank test. A paired Student's t-test was used to measure antibody levels and ratios of antibody response. A probability of $<0.05$ was considered significant.

Example 6

Immunogenicity of dLPS-J5/OMP Vaccine with or without Adjuvant

The ability of the vaccine constructs to induce antibody responses is summarized in Table 1. Antibody responses were tested after three doses of 10 mcg of the vaccine administered 14 days apart as an intramuscular injection. The antibody response to dLPS-J5/OMP alone, with CpG oligodeoxynucleotides, with alum and a combination of CpG oligodeoxynucleotides and alum were investigated. As previously reported (4) the dLPS/OMP vaccine alone was highly immunogenic (P<0.005 versus control group) and well tolerated. The mean antibody concentration was increased 5 fold (P<0.01) by CpG oligodeoxynucleotides. Alum produced a modest increase in the antibody response to the dLPS-J5/OMP vaccine alone but significantly reduced the antibody response to the combination of CpG oligonucleotides plus dLPS-J5/OMP vaccine (P<0.01). Since this reduction in antibody response could be due to interference of alum with epitope processing of the vaccine construct when adminstered along with CpG oligodeoxynucleotides, alum was not used in the vaccine preparation in subsequent studies.

Example 7

Active Protection with dLPS-J5/OMP Vaccine with and without CpG ODN

Animals (n=15/group) were actively immunized in the presence or absence of CpG oligodeoxynucleotides. The control group (n=5) received CpG oligodeoxynucleotides+ saline administered at the same time interval completing the immunization schedule 30 days before CLP.

The results of the CLP experiment are presented in FIG. 1. A second control group received CpG oligonucleotides alone six days prior to CLP (n=5). The dLPS-J5/OMP vaccine group with or without CpG oligodeoxynucleotides provided significant protection from lethality following CLP (P<0.0.1). When given 6 days before CLP, CpG oligodeoxynucleotides provided some protection (4/5 animals survived) but when given alone at the same schedule as the immunizations (i.e. last dose given one month before CLP), there was no survival in this control group (FIG. 1).

Figure 2:
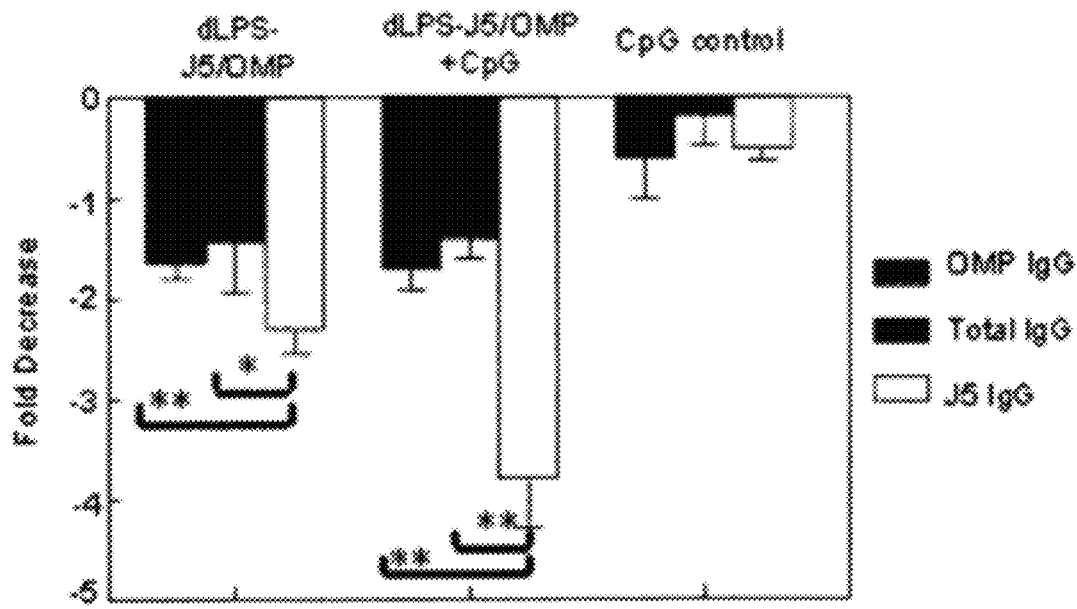
FIG. 2 shows a decrease in geometric mean antibody concentrations as a ratio of specific IgG antibody in immunized mice before and 48 hours after CLP. Open bars—anti-core glycolipid lipopolysaccharide antibody; hatched bars—total IgG immunoglobulin; solid bars—anti-OMP (meningococcal outer membrane protein) antibody ratios.

Serum IgG levels against core LPS were measured 28 days after the final immunization (pre-CLP) and 48 hours following CLP (FIG. 2). While the 20 mcg dosing regimen of the dLPS-J5/OMP vaccine alone was highly immunogenic (mean IgG level of anti-core antibody at 151 g/ml), the co-administration of the vaccine with CpG oligonucleotides increased the antibody titer approximately 3-5 fold to 552 g/ml (P<0.005 vs. dLPS-J5/OMP vaccine alone). The CpG-oligodeoxynucleotides control group had a flat antibody response with anti-core antibody levels remaining at baseline values of 0.12 g/ml. The CpG+saline control group all succumbed to polymicrobial intra-abdominal sepsis following CLP (FIG. 1). The dLPS-J5/OMP vaccine group with or without CpG oligodeoxynucleotides were highly protected from lethality after CLP (P<0.01).

The plasma lipopolysaccharide levels were significantly lower in the dLPS-J5/OMP vaccine groups with or without CpG oligonucleotides and peritoneal lipopolysaccharide levels trended lower in the vaccine groups compared to the control group (Table 2). Bacterial concentrations in organ samples were reduced in the vaccine groups compared to the control group. Peritoneal, but not plasma, TNF levels were significantly reduced following CLP in the vaccine group (P<0.01). Gram-negative bacterial counts, TNFa and LPS levels within the peritoneum were lowest in the vaccine+ CpG oligodeoxynucleotides group but were not sufficiently different from values measured in the dLPS-J5/OMP vaccine group to reach statistical significance as shown in Table 2.

TABLE 2

Active Immunization of mice (CLPmodel) with anti-core glycolipid vaccine

| | | | | P value* |
|---|---|---|---|---|
| Plasma endotoxin (ng/ml) | 7.75.5 | 0.20.12 | 1.81.6 | <.001 |
| Plasma TNF** (pg/ml) | 32.010 | 11.67.9 | 18.15.8 | ns |
| Organ cultures (CFU/mcg) | 350774 | 4097 | 031 | <.05 |
| Peritoneal TNF (pg/ml) | 52.63.0 | 23.3 6 | 15.04.5 | <.01 |
| Peritoneal endotoxin (ng/ml) | 92.444 | 10.632 | 3.19 | 0.1 |

P values represent differences (mean +/− sem) between control vs. either vaccine group (with or without CpG-ODN's). No significant differences were found between the two vaccine groups If a mechanism of action of the anti-core glycolipid antibodies was to bind and promote the clearance of bacteria by the reticulo-endothelial system, then serum antibodies against core glycolipid and not anti-OMP antibodies would be decreased. This depletion of anti-core glycolipid antibody could be due to a generalized decrease in IgG (e.g. hypermetabolic state during sepsis) or to a depletion in specific antibody (as may occur with the binding of antigen and subsequent clearance of the complex). Although a brisk antibody response to the OMP component of the vaccine complex was observed following immunization, the levels of IgG specific for OMP 48 hr post CLP was only mildly reduced (1-2 fold pre-CLP levels). This level of reduction in IgG specific for OMP was comparable to the ratio of total IgG levels before and after CLP (FIG. 2).

In contrast, serum anti-core lipopolysaccharide IgG levels were significantly depleted 3-4 fold 48 hours after onset of intra-abdominal sepsis. This reduction in antibody levels was specific for the target epitopes found within the core oligosaccharide portion of the vaccine formulation. As expected the administration of CpG oligodeoxynucleotides alone at the same vaccine schedule induced minimal IgG antibody responses to either OMP or core glycolipid.

Example 8

Protection Against Select Agents with dLPS-J5/OMP Vaccine with CpG ODN

Figure 3A:
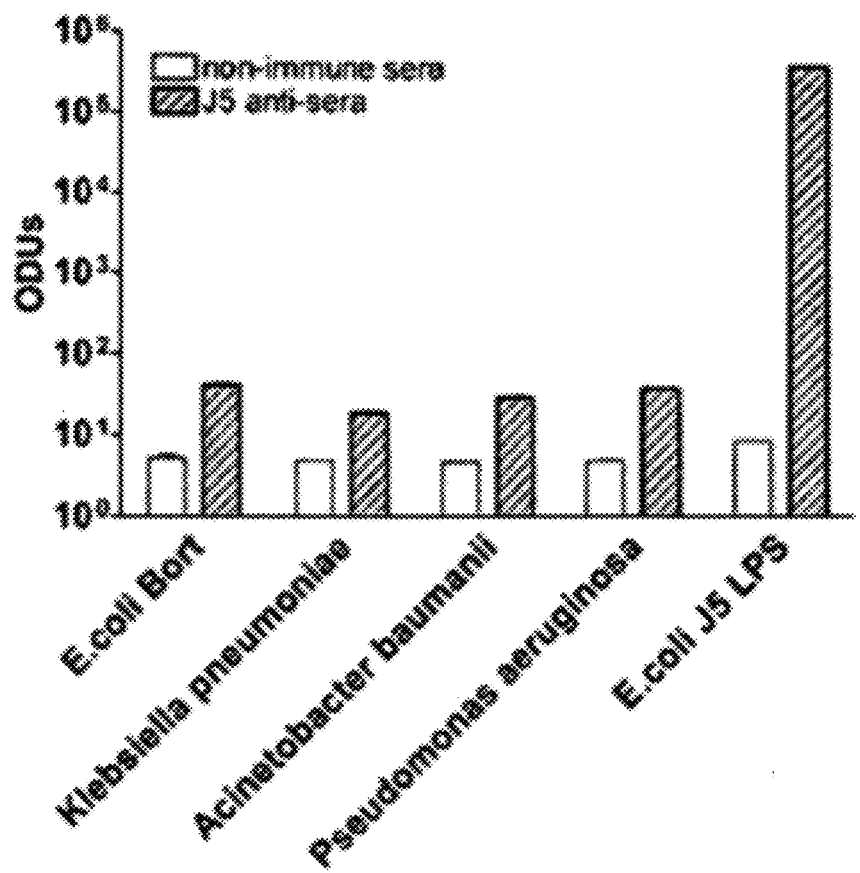
FIGS. 3A-3B show that the antibody induced by the vaccine was able to bind to various select agents and to whole bacteria.
Figure 3B:
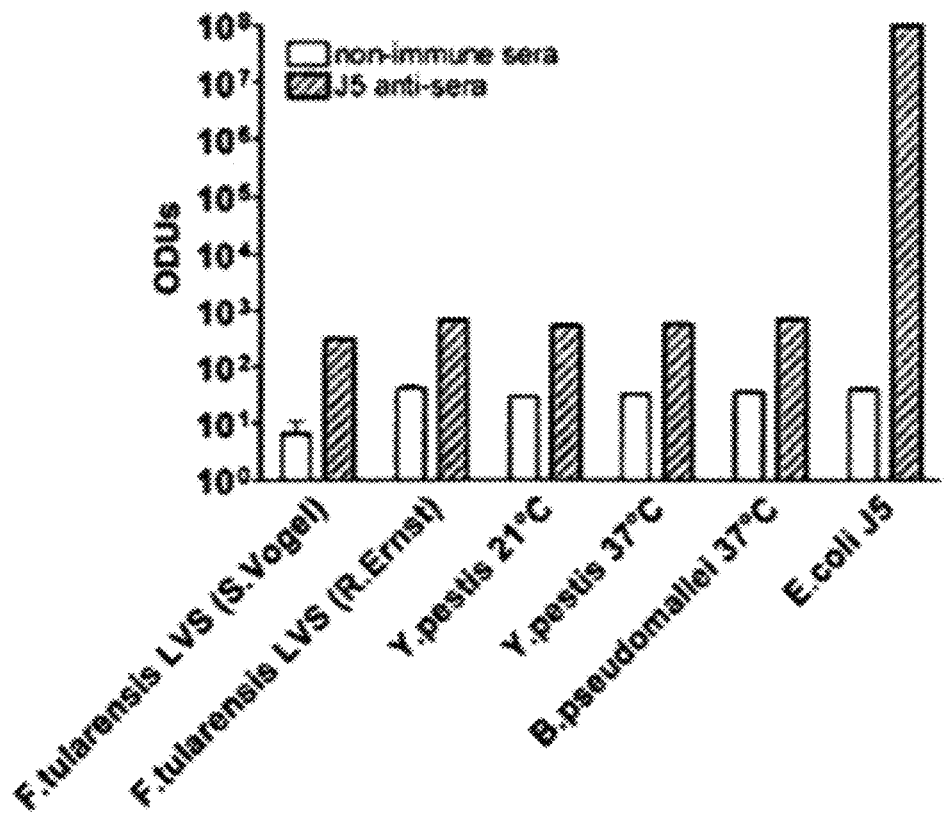
Figure 4A:
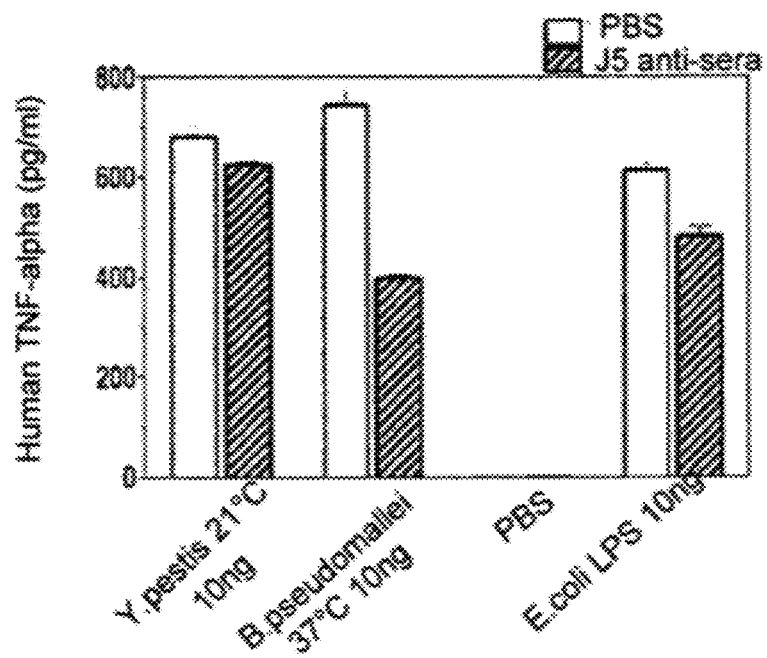
FIGS. 4A-4E shows the data from ex vivo functional assay that was performed using whole blood.
Figure 4B:
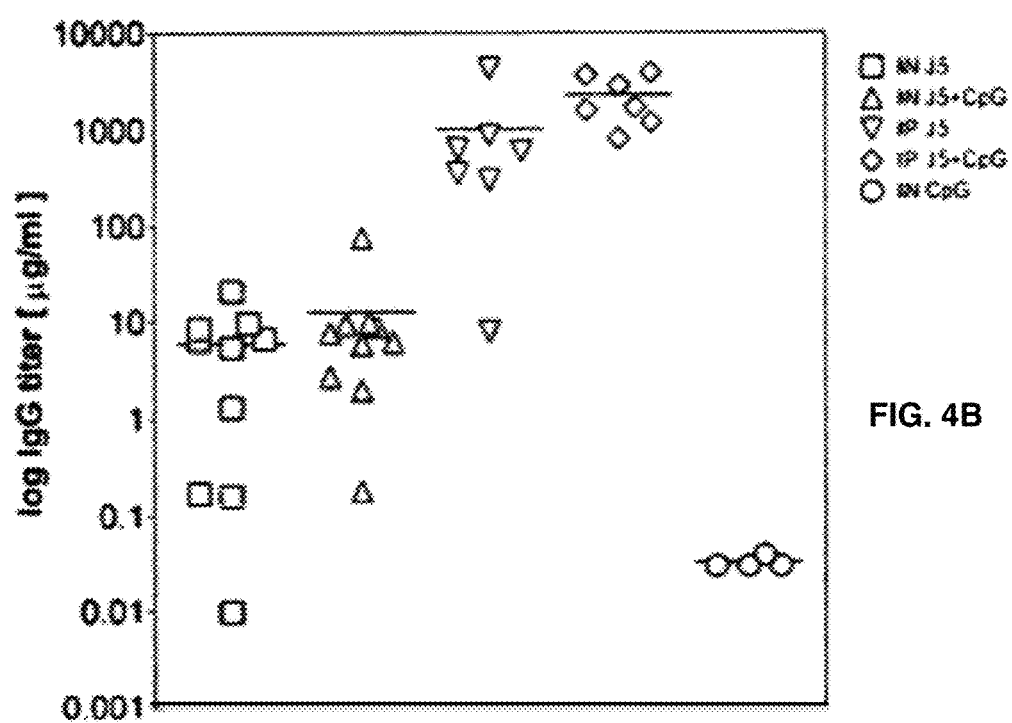
Figure 4C:
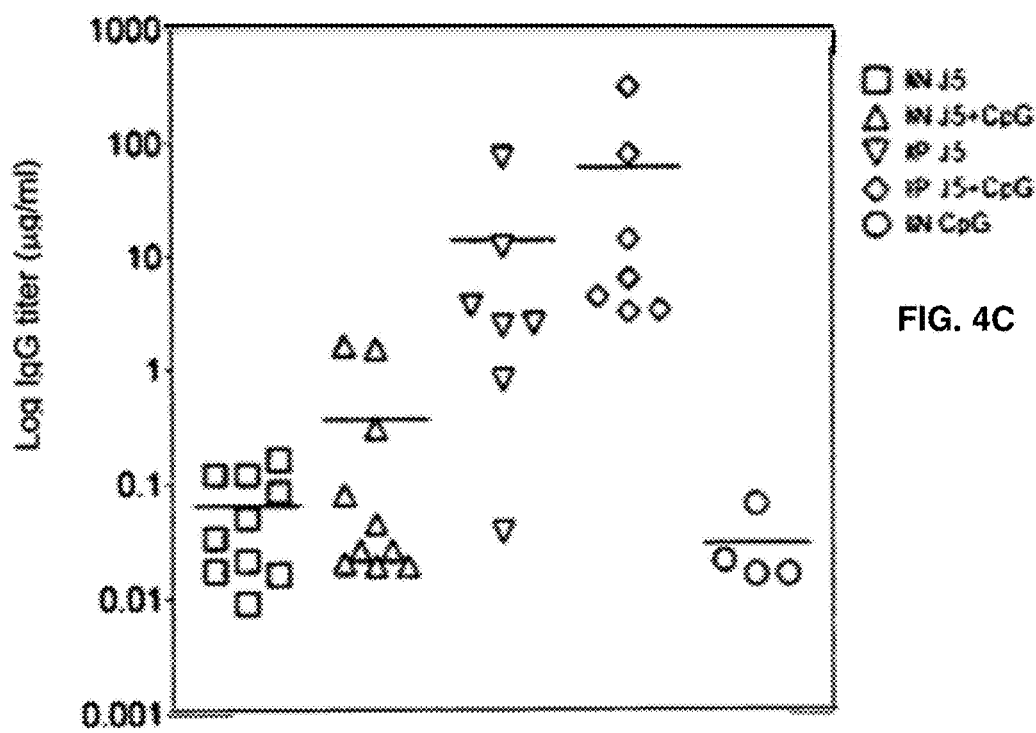
Figure 4D:
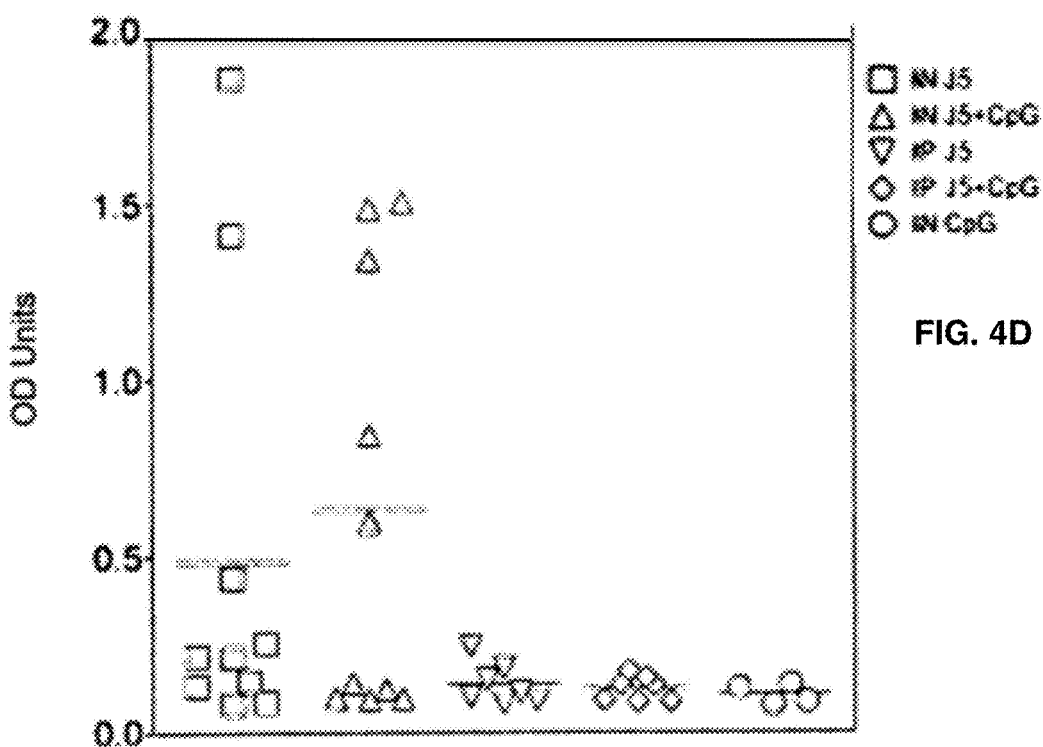
Figure 4E:
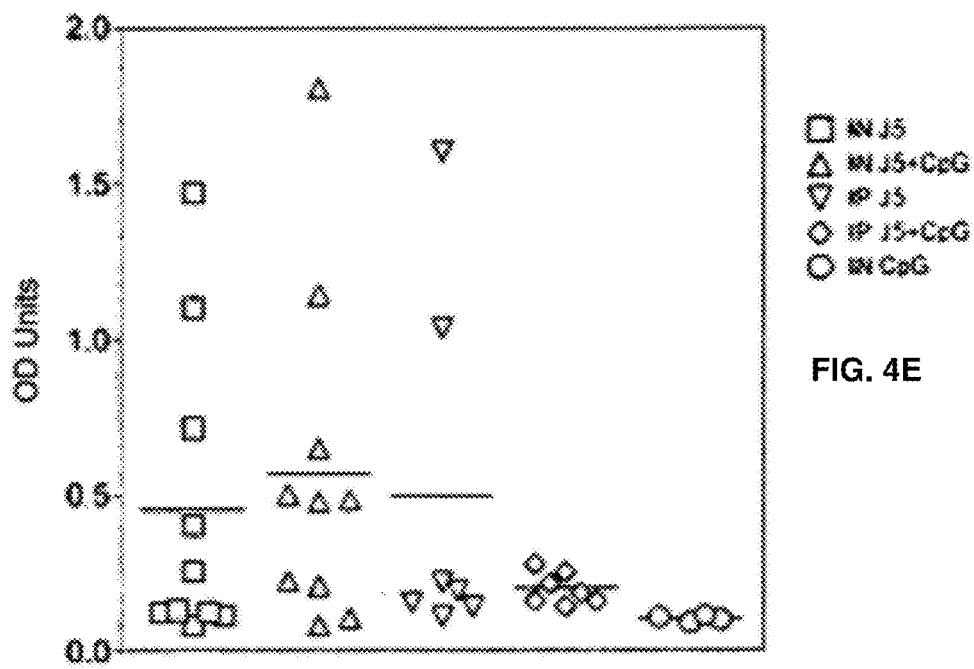
Figure 5:
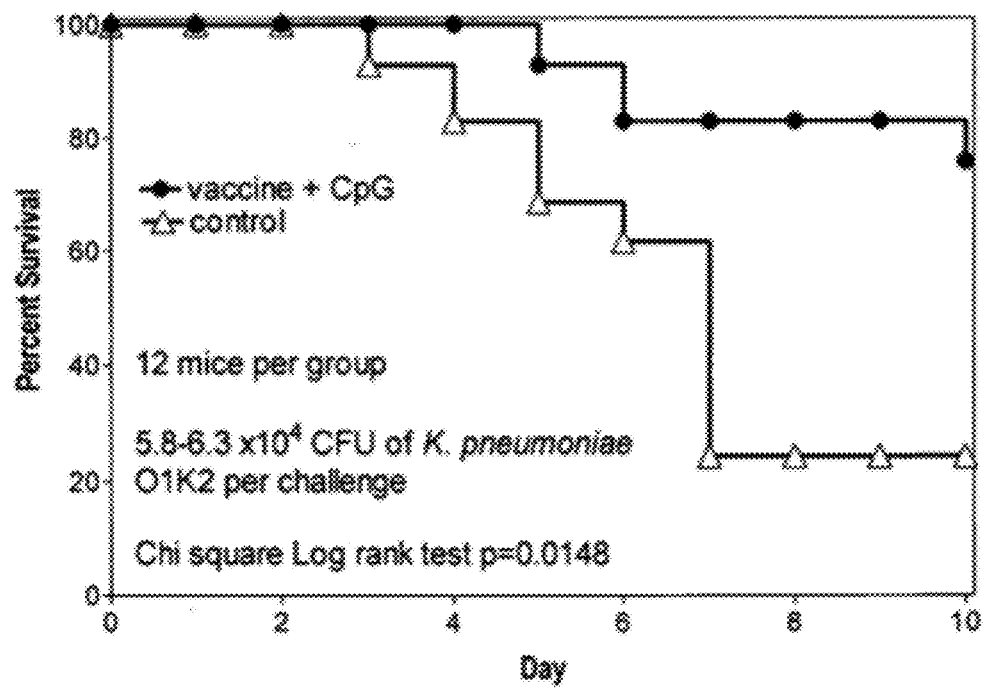
FIG. 5 shows the effect of the vaccine after intratracheal challenge.

The antibody induced by the vaccine of the present invention bound to both the LPS of the various select agents (FIG. 3B) shown in the figure as well as to the whole bacteria (FIG. 3A). In the ex vivo assay (FIG. 4A), the various LPS preparations were added to heparinized human whole blood, incubated the mixture overnight and then measured cytokine levels in the plasma. The effect on cytokines induced by *Burkholderia* (the agent of melioidosis) was quite substantial. There was no effect on the LPS of *francisella* since that LPS had very limited endotoxic activity (if any). The present invention also showed that the antibody induced by the vaccine bound to a highly antibioitic-resistant strain of actinobacter, which has been the scourge of ICU units nationwide, and has forced clinicians to use old, highly toxic antibiotics. The present invention also demonstrated the effect of the various combinations of the vaccine preparations on the serum and the BAL IgA and IgG levels (Table 3; FIGS. 4B-4E). Additionally, the present invention also demonstrated the effect of the vaccine after intratracheal challenge (FIG. 5). The vaccine and CpG construct was immunoprotective when mice were challenged with *K. pneumoniae*.

TABLE 3

Effect of the Vaccine preparations on the Serum and BAL IgG and IgA levels

|  | N | Serum IgG (µg/ml) | %* | Serum IgA (OD**) | %* | BAL IgG (µg/ml) | %* | BAL IgA (OD**) | %* |
|---|---|---|---|---|---|---|---|---|---|
| IN J5 | 10 | 6.6 ± 2.1 | 70 | 0.48 ± 0.20 | 30 | 0.06 ± 0.02 | 30 | 0.45 ± 0.15 | 40 |
| IN J5 + CpG | 10 | 13 ± 7.1 | 90 | 0.63 ± 0.20 | 50 | 0.36 ± 0.20 | 30 | 0.57 ± 0.17 | 60 |
| IP J5 | 7 | 1000 ± 560 | 100 | 0.12 ± 0.01 | 0 | 14 ± 10 | 86 | 0.50 ± 0.22 | 29 |
| IN J5 + CpG | 7 | 2300 ± 470 | 100 | 0.14 ± 0.02 | 0 | 60 ± 43 | 100 | 0.20 ± 0.02 | 0 |
| IN CpG | 4 | 0.03 ± 0.002 |  | 0.11 ± 0.01 |  | 0.03 ± 0.01 |  | 0.10 ± 0.01 |  |

Antibody levels expressed as mean ± standard error;
*% responders with antibody titers ≥4x control (IN CpG);
**OD is optical density of neat serum at A450 nm

Example 9

Protection Against Heterologous Gram-Negative Bacterial Pneumonia by Intranasal Administration of a Detoxified Endotoxin Vaccine The vaccine used in all experiments was the previously characterized J5dLPS-OMP, containing 100 µg/ml of LPS and 136 µg/ml of OMP by weight (4). The adjuvant CpG ODN 2006 was obtained from Coley Pharmaceutical Group (Ottawa, Canada). The highly virulent *Klebsiella pneumoniae* O1:K2 strain was originally obtained from Drs. Ida and Frits Orskov, WHO *E. coli* and *Klebsiella* Reference Center (Statens Seruminstitut, Copenhagen, Denmark); the $LD_{50}$ in outbred ICR mice was $\sim 1 \times 10^4$ CFU. The *Pseudomonas aeruginosa* (strain PA01) was obtained from Dr. Gerald B. Pier (Boston, Mass.).

Mouse Vaccination

Female outbred white mice (Crl:CD-1(ICR)BR, 6-8 week old, Charles River, Wilmington, Mass.) were vaccinated with 1 µg of J5dLPS-OMP (by LPS weight) either i.n. or i.p. on weeks 0, 2, and 4. The i.n. administration of 25 µg CpG preceded i.n. vaccination with J5dLPS-OMP by 30 minutes to one hour to allow mucosal absorption. The i.n. administration of saline, CpG, or J5dLPS-OMP was given in a liquid volume of 5 µl into each nostril (10 µl total volume). The i.p. vaccinations were given as a single injection in a total volume of 200 µl. All dilutions were performed with sterile endotoxin-free PBS (Biosource International, Rockville, Md.). All experiments were approved by and conducted in compliance with the Institutional Animal Care and Use Committee of the University Of Maryland School Of Medicine.

Mouse Pneumonia Model

The day prior to challenge, frozen bacteria, stored in 10% casein stocks at −20° C., were streaked onto trypticase soy agar (TSA) plates and incubated overnight at 37° C. On the day of challenge, single colony isolates were grown to mid-log phase in trypticase soy broth (TSB) at 37° C. on orbital shaker prior to washing and resuspending the cell pellet in sterile PBS to the desired challenge concentration. The actual inoculum of the challenge dose was confirmed by colony counts on TSA plates.

After at least two weeks from the last vaccination lethal doses of a previously described *Klebsiella* O1:K2 (42) were administered by a tongue-pull method to the lower respiratory tract (i.e. intratracheal (IT) route). Mice were anesthetized with isoflurane (Baxter; Deerfield, Ill.) prior to the deposition of 50 µl bacterial suspension to the posterior oropharynx. A successful challenge was confirmed by aspiration of the bacterial suspension and audible crackles. This method allowed us to deliver a consistent inoculum to each mouse. Each mouse was weighed daily until death or until they ceased to lose weight over 2 consecutive days and demonstrated signs of improvement (e.g. increased activity). Those still surviving at 14 days were euthanized and bacterial organ counts were performed. The peak percent weight loss for each mouse was calculated from the lowest post-challenge weight, prior to recovery or death, and the initial weight the day of the IT challenge.

Serum and BALF

In separate prospectively designated mice, serum and bronchoalveolar lavage fluid (BALF) was obtained two weeks after the third vaccination (day 42). Whole blood was obtained by cardiac puncture, after euthanization, and serum was stored at 4° C. The collection of BALF was performed by cannulation of the trachea and gentle lavage of the lungs with a single round of 1 ml sterile PBS. Both serum and BAL fluid were stored at 4° C. until analysis was performed, usually within 1 week.

ELISA for Anti-CGL Antibody

Serum and BALF samples were measured for anti-CGL IgG and IgA antibody levels as described (3). ELISA IgG antibody titers were calculated from a standard curve created from mouse monoclonal IgG antibody (Sigma) when comparing the optical density at $A_{450}$ from the linear portion of the curve. ELISA IgA antibody titers were expressed as optical density units (ODU) calculated by multiplying the dilution factor by the optical density at $A_{450}$ from the linear portion of the curve. Values were considered non-detectable (ND) if they were below the limits of detection for the assay (<10 ng/ml). A vaccine "responder" was defined as an antibody level that was ≥4 times that of the control.

Macrophage Killing Assay

Macrophages were cultured according to our previously described methods (43). Primary peritoneal macrophages (PM) were obtained from naïve ICR mice 4 days after i.p. inoculation of 3% Brewer Modified Thioglycollate Medium (Becton Dickinson, Cockeysville, Md.). Alveolar macrophages (AM) were obtained from matched naïve ICR mice after four rounds of flushing the lungs with 1 ml PBS. In our hands, the recovered cells typically consisted of >98% viability by Trypan Blue Dye exclusion and >95% macrophages as determined by immunofluorescence using the F4/80 macrophage marker (44) Peritoneal or BAL fluid cell suspensions from mice were pooled and adjusted to $1 \times 10^6$ macrophages per ml in culture medium containing RPMI-1640 (Gibco-BRL, Frederick, Md.) with 5% fetal bovine serum (FBS; Atlanta Biologicals, Lawrenceville, Ga.), and rested in polypropylene tubes (Elkay Products, Inc. Shrewsbury, Mass.) in 5% $CO_2$ at 37° C. overnight.

Bacterial suspensions were freshly made from frozen stocks for each experiment as in the mouse pneumonia experiments. Bacteria, between $10^5$-$10^6$ CFU/ml, were opsonized by incubating at 4° C. for 30 min on rotator with an equal volume of un-diluted immune serum, immune BALF, control BALF, or sterile PBS (mock treatment).

Macrophage-mediated killing by nitric oxide production was inhibited with 1 uM L-N$^6$-(1-iminoethyl)lysine (L-NIL, Sigma). To determine macrophage-mediated killing at different time points, individual tubes containing infected macrophages were centrifuged at 380×g for 10 minutes after incubation for 1, 5, and 24 hours. Cells were lysed with 1 ml of cold sterile distilled water at 37° C. for 30 min, vortexed, and plated on TSA for the viable bacterial counts. The killing activity was measured by calculating the log difference in counts from time 0 to 1, 5 and 24 hours.

Statistical Analysis

Antibody ELISA results for both serum and BAL were expressed as arithmetic means with the standard error. Differences were analyzed by a non-parametric Kruskal-Wallis one-way analysis of variance for comparison of multiple groups or the Mann Whitney test for comparison of two groups. The survival functions of each vaccination group were expressed using Kaplan-Meier survival plots, and differences in survival were compared using the Logrank test. Macrophage-mediated log reductions were analyzed by the Student's t test. Results were considered significant with two-sided P values <0.05. GraphPad Prism version 4.0 (San Diego, Calif.) was used to perform these statistical calculations.

Results

Figure 6A:
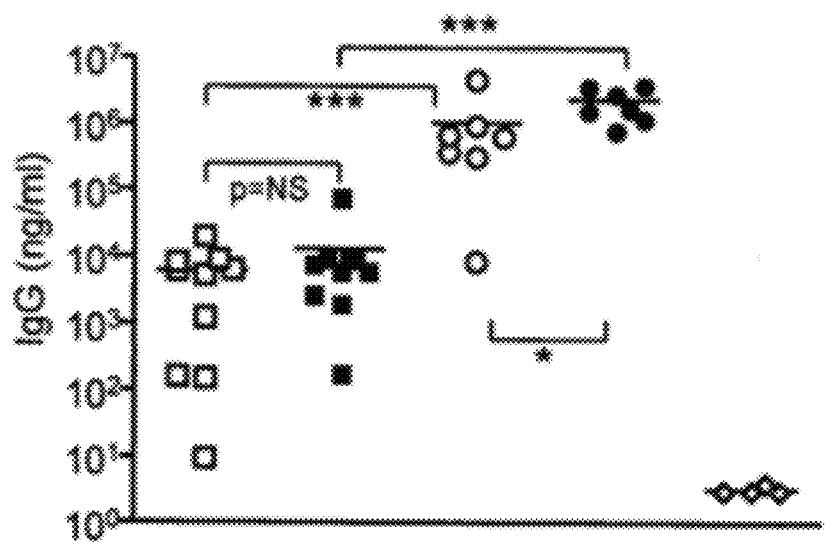
FIGS. 6A-6D show effect of J5dLPS-OMP (J5) in female outbred white (Cr1:CD-1(ICR)BR) mice. Mice were immunized with 1 µg of J5dLPS-OMP (J5) at weeks 0, 2 and 4±25 µg of CpG at week 0. BALF and serum was collected at week 6. ELISA anti-CGL antibody responses are illustrated in the bar graphs as arithmetic mean and 95% CI for serum IgG (FIG. 6A), BALF IgG (FIG. 6B), serum IgA (FIG. 6C) and BAL IgA (FIG. 6D) responses. *$p<0.05$, $p<0.01$, *$p<0.001$ by Mann-Whitney test. ND=non-detectable, IN=intranasal, IP=intraperitoneal.

Following immunization, all mice demonstrated similar weight gain and had no overt adverse effects over 6 weeks. Mice immunized with i.n. CpG alone had anti-CGL antibody levels that were near the limits of detection of the assay. Mice immunized with PBS alone also had anti-CGL antibody levels that were near the limits of detection [DNS]. All mice that received i.p. vaccination had robust systemic IgG responses, regardless of whether CpG was used. Mice vaccinated with J5dLPS-OMP plus a single dose of CpG via the i.p. route showed statistically higher systemic (serum) anti-CGL IgG antibody titers than mice that were similarly vaccinated via the i.n. route (FIG. 6A). When J5dLPS-OMP was administered i.n., alone or with CpG, mice achieved a mean serum IgG antibody level approximately 100-fold lower than that achieved by i.p. vaccine administration (without CpG). The addition of CpG resulted in a doubling of serum IgG antibody regardless of the route of administration. Therefore, a single dose of CpG in a multi-dose immunization regimen modestly increased the antibody response.

Figure 6B:
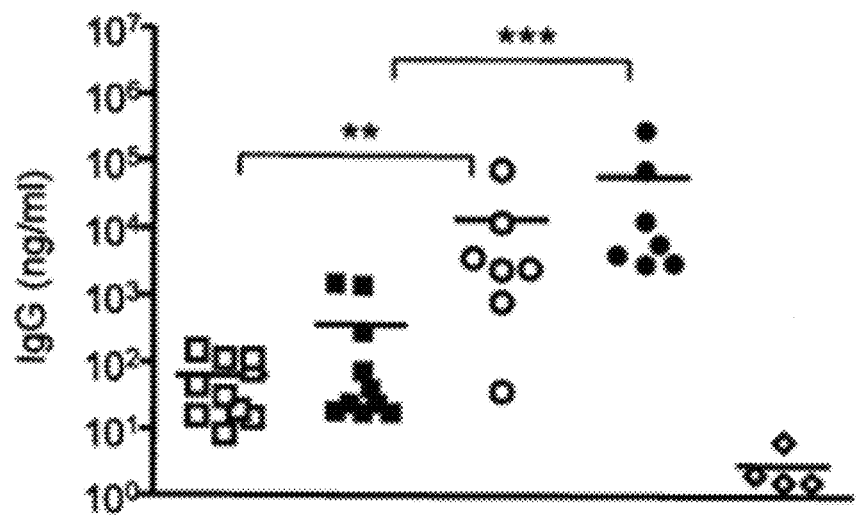

When examining BALF, i.p. vaccinated mice likewise had significantly higher IgG antibody levels than i.n. immunized mice (FIG. 6B). Unlike the doubling observed in serum, the addition of CpG resulted in a 4-fold increase in BAL IgG antibody response when the vaccine was administered by either route. The i.p. route of administration resulted in 86-100% BALF IgG responders in comparison to 30% responders when delivered by the i.n. route of administration.

Figure 6C:
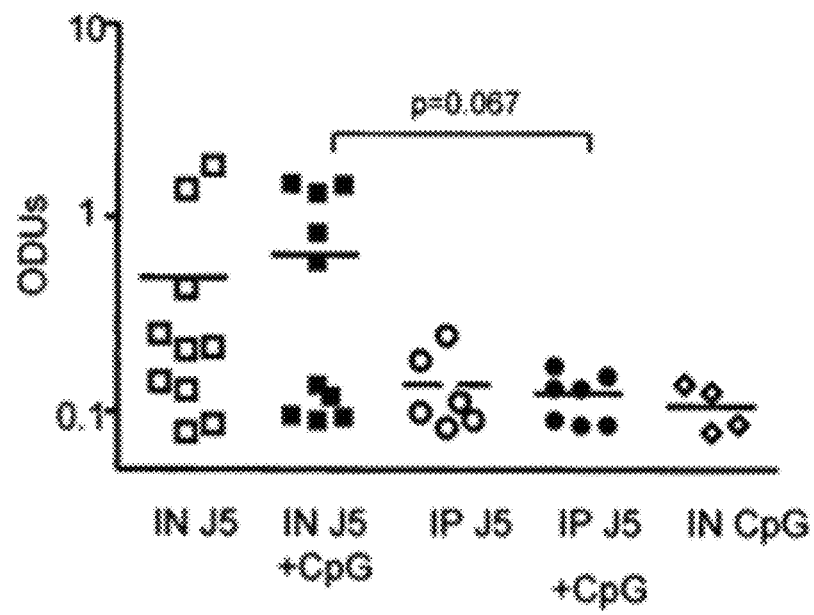

Since IgA might be important as a first line of defense against mucosal infections, such as GNB pneumonia, we measured the anti-CGL IgA antibody levels in both the serum and BAL fluid samples after immunization by both routes of administration. Mice that received J5dLPS-OMP i.p. alone had little serum anti-CGL IgA and the addition of CpG had did not increase the serum IgA antibody responses (FIG. 6C). In comparison, mice that were given J5dLPS-OMP by i.n. route of administration had modest serum IgA antibody responses; there was a trend toward higher IgA responses with the addition of CpG but this did not achieve statistical significance.

Figure 6D:
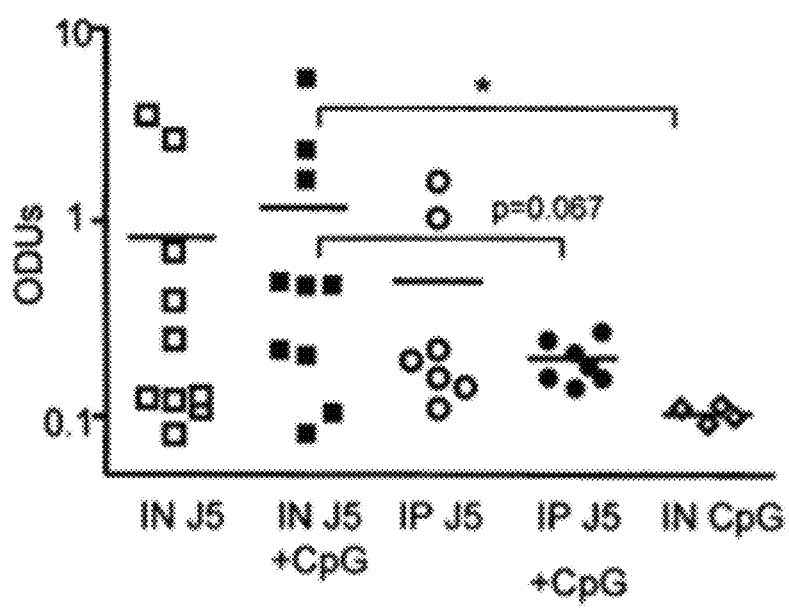

The BAL IgA for mice that were immunized i.p. with J5dLPS-OMP alone or with CpG was lower than mice that received vaccination by i.n. route of administration (FIG. 6D). Two of 7 mice that received i.p. vaccine alone had elevated IgA antibodies, but none of 7 mice that received i.p. vaccine plus CpG had elevated IgA antibodies. Thus, i.n. vaccination is superior to i.p. vaccination for the induction of IgA antibody responses.

Since a single dose of CpG was an effective immunoadjuvant for our vaccine, we speculated that concomitant administration of CpG with each of the three doses of J5dLPS-OMP might increase the chance for each mouse to mount local and systemic antibodies. However, we found that two or three doses of CpG compared to a single dose did not significantly improve either serum or BAL IgG and IgA anti-CGL responses when given by intramuscular, subcutaneous, or intraperitoneal routes of administration (DNS).

A murine model of pneumonia, using the tongue-pull IT route of administration, was used to evaluate whether i.n. vaccination with J5dLPS-OMP might be effective in protection against lethal GNB pneumonia. It was consistently observed 100% lethality with *Klebsiella* O1:K2 in ICR mice at doses 10$^6$ CFU, >80% lethality at 10$^5$ CFU, 50% lethality at just under 10$^4$ CFU, and no lethality at 10$^3$ CFU. Therefore the target dose for challenge experiments was ~5×10$^4$ CFU, the linear portion of the lethality curve. Using this target dose in outbred mice resulted in progressive illness over 96 hours with death typically occurring between 5 and 8 days post-challenge. This *Klebsiella* isolate rapidly multiplied in vivo; predictably 10$^6$ CFU per gram of lung tissue and 100-1000 CFU per ml of blood were recoverable within the first 24 hours after infection. At 96 hours post-infection mice had 10$^7$ CFU per gram of lung tissue, 10$^4$-10$^5$ CFU per ml of blood, and 10$^5$-10$^6$ CFU per gram of extra-pulmonary tissue, i.e. liver and spleen.

Figure 7A:
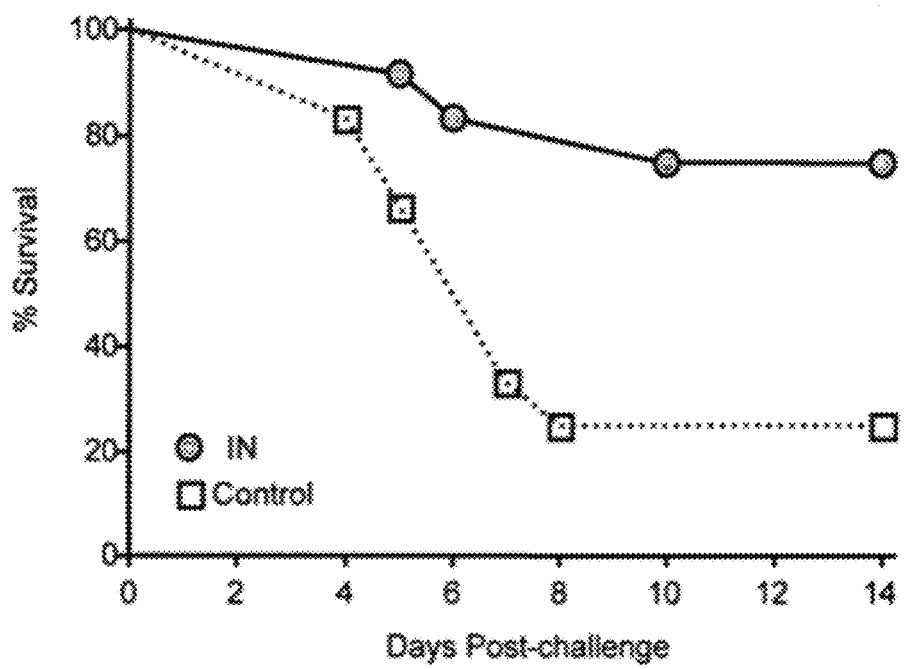
FIGS. 7A-7B shows Kaplan Meier survival curves from the sum of two intratracheal (IT) challenge experiments. Mice were immunized with 1 µg of J5dLPS-OMP and 25 µg of CpG on weeks 0, 2 and 4 and challenged IT with *Klebsiella pneumoniae* E1757 at $5.8$-$6.3\times10^4$ CFU per mouse at week 6. 12 mice per group received i.n. J5dLPS-OMP with CpG (IN) or i.n. PBS (control). *$p=0.0148$ by Log rank test.
Figure 7B:
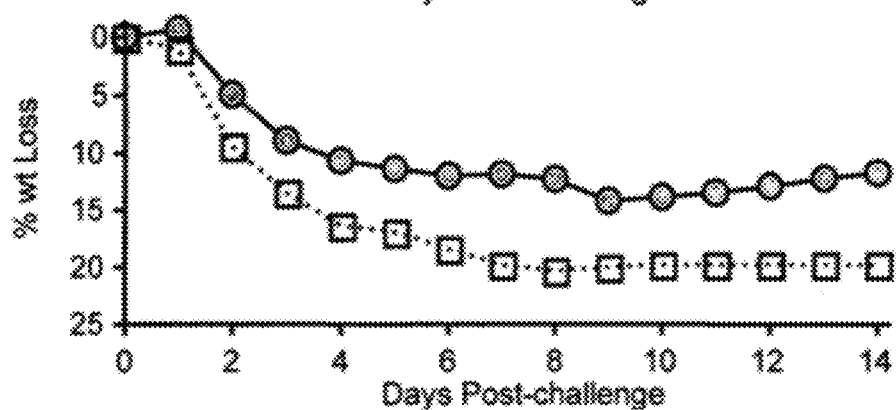

In two separate challenge experiments, mice were immunized with 3 i.n. doses of J5dLPS-OMP plus CpG and compared to administering PBS alone and all mice were challenged weeks later. In pilot studies mice vaccinated with CpG alone failed to demonstrate a survival benefit compared to saline (DNS). Two weeks after the third vaccination, IT challenges with *Klebsiella* O1:K2 at 5.8 and 6.3×10$^4$ CFU/mouse were performed in the two experiments, respectively. Vaccinated mice showed improved survival when compared to control mice (p=0.015, Logrank test) (FIG. 7A). All surviving mice had complete clearance of bacterial infection as documented by the absence of culturable bacteria from the lungs and at distal sites at 10 days post-challenge, except for a single well-appearing mouse from the vaccinated group which at sacrifice was found to have 9×10$^6$ CFU/ml in the lung, 2700 CFU/ml from spleen and no bacteria recovered from the liver. All mice that died had very high organ bacterial counts, >10$^8$ CFU per gram of tissue. The severity of pneumonia, as assessed by change in weight, trended toward less weight loss in the vaccinated mice (FIG. 7B). Note that in order to graph some censored data, the weights of mice that died after the date of death were plotted using the weight at death; by day 8 post-challenge in the control group only 3 surviving mice contribute to the curve. The peak percent weight loss was calculated to compare the changes in weight, of each group, irrespective of whether individual mice lived or died. Mice immunized i.n. had 15.9% (95% Cl 10.1-21.7) peak percent weight loss in comparison to 20.9% (95% Cl of 16.1-25.5) in the control (PBS) group; not statistically different.

Figure 8A:
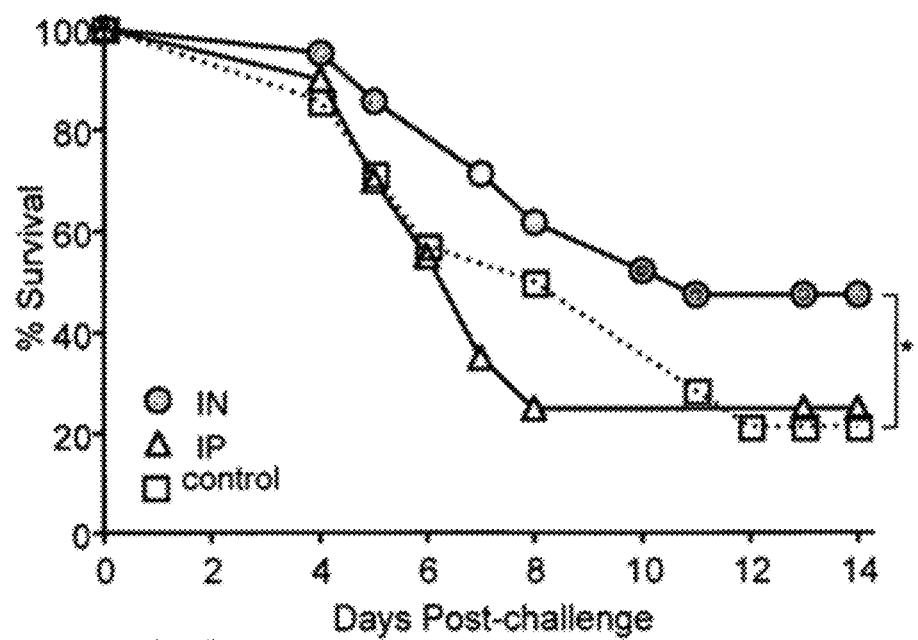
FIGS. 8A-8B show Kaplan Meier survival curves from the sum of three IT with *Klebsiella pneumoniae* E1757 at $7.6$-$9.5\times10^4$ CFU per mouse at week 6. 21 mice received i.n. J5dLPS-OMP with CpG (IN), 20 mice received i.p. J5dLPS-OMP with CpG (IP) and 14 mice received i.n. PBS (control). *$p=0.047$ by Log rank test.
Figure 8B:
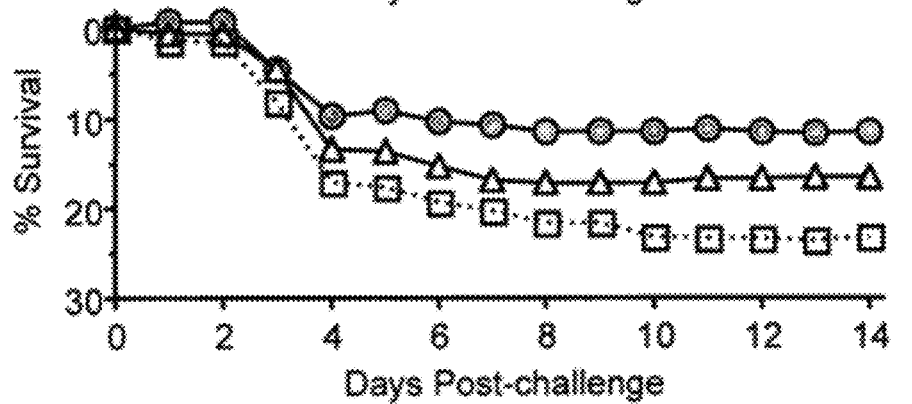

To assess whether i.n. vaccination might be superior to i.p., we immunized mice i.n. or i.p. with the same biweekly 3 dose regimen (vaccine+CpG). In three separate experiments with IT challenge doses of *Klebsiella* O1:K2 at 7.6, 9.5, and 7.6×10$^4$ CFU/mouse, respectively, we observed protection in i.n. vaccinated mice (p=0.047, Logrank test) and no protection in i.p. vaccinated mice (FIG. 8A) when compared to control (PBS only) animals. There was a delayed time to death among i.n. immunized mice (median survival of 11 days) in comparison to i.p. immunized (median survival of 7 days) and control animals (median survival of 9.5 days) The severity of pneumonia by weight loss for i.n. immunized mice was less than i.p. vaccinated mice and control mice (FIG. 8B). The peak percent weight loss was 14.0% (95% CI 10.1-17.9) in the IN group, 17.4% (95% CI 12.7-22.1) in the IP group, and 24.7% (95% CI 19.4-30.1) in the control group; significant differences were observed between the i.n. immunized and control group, but not between i.p. immunized and controls.

Given the survival benefit and reduced organ bacterial load among immunized mice, it is hypothesized that the vaccine induced antibodies that enhanced the uptake and killing of bacteria by macrophages. In the macrophage killing assay, freshly isolated primary macrophages were allowed to phagocytose and kill bacteria that were pre-opsonized by heat inactivated serum or BALF samples from control and immunized mice. A single representative "high titer" immune BALF sample (ELISA IgG=200 ng/ml, IgA=1.8 ODU), "low titer" control BALF sample (ELISA IgG=1 ng/ml, IgA=0.7 ODU), and a "high titer" immune serum sample (ELISA IgG of 230 mg/ml, no IgA) was selected for the following in vitro assays.

Figure 9A:
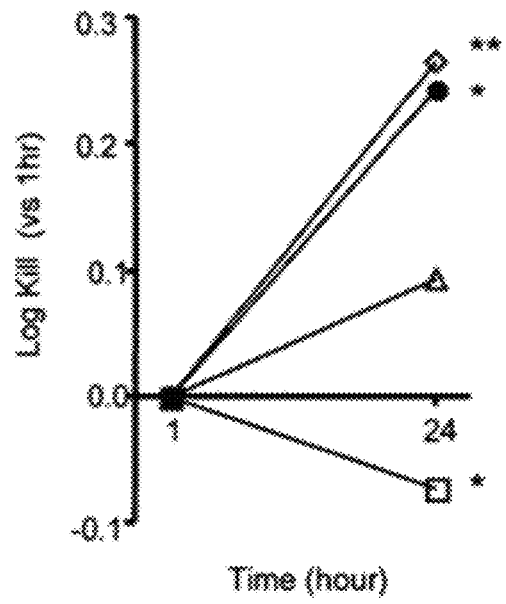
FIGS. 9A-9C show bacterial counts that were assessed after freshly harvested primary macrophages were mixed with pre-opsonized bacteria using "high titer" immune serum, "high titer" immune BALF or "low titer" control BALF; each sample was derived from a mouse that received active immunization i.p. or i.n. or received i.n. CpG alone, respectively. Sterile PBS was used as mock pre-opsonization, designated as untreated bacteria. At 24 hours, peritoneal macrophages (PM, $10^6$) demonstrated enhanced killing of *Klebsiella pneumoniae* O1:K2 (MOI 1:10, $10^5$ CFU) (FIG. 9A) and *Pseudomonas aeruginosa* PAO1 (MOI 1:1, $10^6$ CFU) (FIG. 9B) and alveolar macrophages (AM), $10^6$) demonstrated a trend toward enhanced killing on *Pseudomonas aeruginosa* PAO1 (MOI 1:1, $10^6$ CFU) (FIG. 9C). Data are expressed as means from experiments with comparisons for significance calculated against the control BALF responses. NS=not significant, *$p<0.05$, $p<0.01$, *$p<0.005$ by two-tailed Student's t test.

The killing capacity of PM on *Klebsiella* O1:K2 was examined at 24 hours in three independent experiments with each containing two replicates at each time point. (FIG. 9A) Immune BALF mediated greater killing in comparison to control BALF or untreated bacteria. Immune serum also mediated greater killing in comparison to control BALF and untreated bacteria and was statistically superior to that of immune BALF. Control BALF mediated a moderate amount of killing in comparison to untreated bacteria; suggesting that additional non-immunoglobulin, non-complement opsonization may have a role.

Figure 9B:
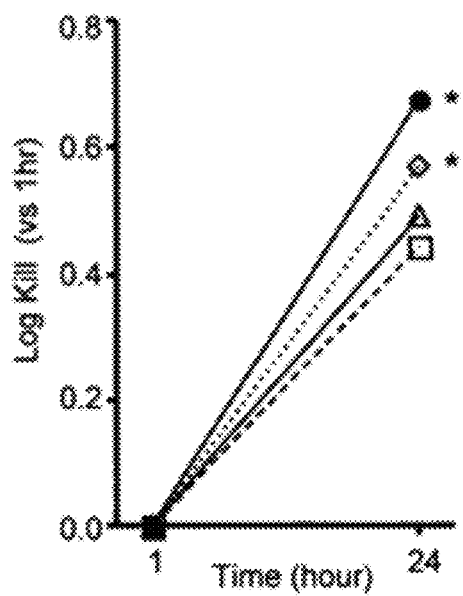

Since the vaccine was designed to elicit antibodies against conserved epitopes in GNB, the ability of these antibodies to enhance the killing of another heterologous GNB, *Pseudomonas aeruginosa* (PA01), was tested in two separate experiments conducted in duplicate. Killing was assessed at 24 hours with PM infected with PAO1 that was pre-opsonized with the same serum and BALF samples as in the previous experiments. (FIG. 9B) Immune BALF and immune serum elicited significantly higher killing than either control BALF or untreated bacteria The opsonic activity of control BALF was not significantly different from no treatment.

Figure 9C:
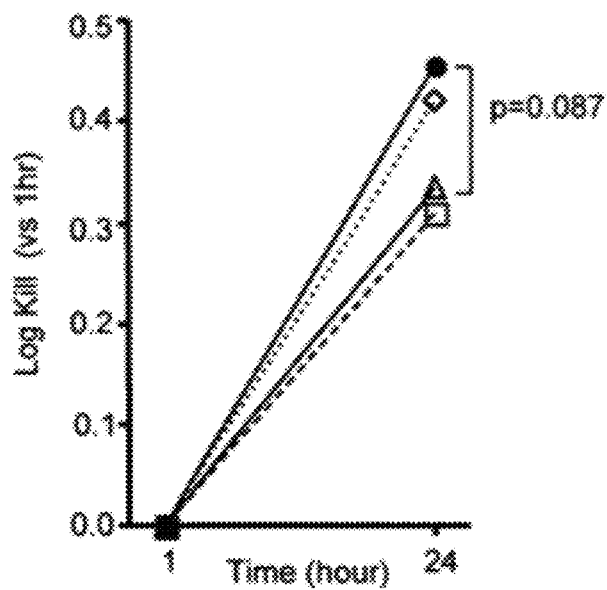

Since AM may be more relevant to the pneumonia model, we measured the killing function of AM on PAO1, in two separate experiments conducted in duplicate. The highest killing activity was found with immune BALF followed by intermediate killing with immune serum treated bacteria; however neither treatment achieved statistical difference from control BALF treated bacteria (FIG. 9C). The control BALF was not different from untreated bacteria.

Figure 10:
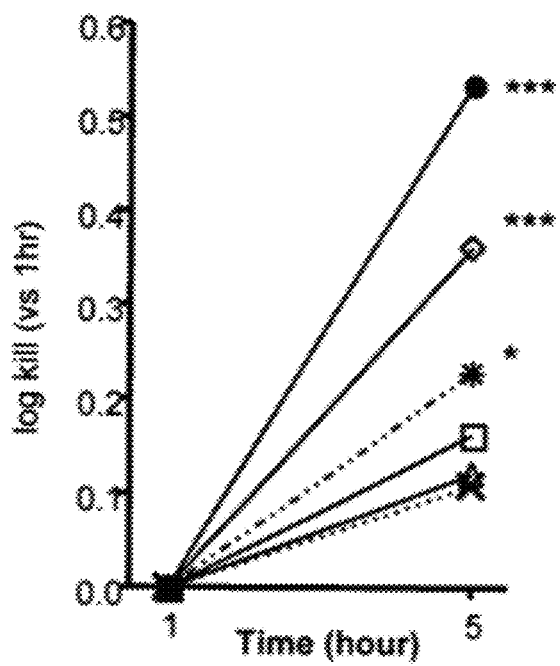
FIG. 10 shows the bacterial counts at 5 hours that were assessed using freshly harvested primary PM ($10^6$) and PAO1 (MOI 1:1, $10^6$ CFU) that had been pre-opsonized with the same immune serum, immune BALF, or control BALF as discussed supra. The immune serum was diluted 1000 fold in order to approximate the anti-CGL IgG in the immune BALF. L-NIL was added to PM that were infected with PAO1 pre-opsonized with immune serum to inhibit nitric oxide-mediated macrophage killing. Data are expressed as means from two independent experiments conducted in duplicate and comparisons that were calculated against the control BAL response. NS=not significant, *$p<0.05$, ***$p<0.005$ by two-tailed Student's t test.

In order to further dissect out the potential role of anti-CGL antibody opsonization of bacteria on macrophage-mediated killing, two separate experiments with duplicates of each condition were conducted as in the previous experiments using immune serum that was diluted 1000-fold (with sterile PBS) in order to mimic the concentration of anti-CGL IgG in the immune BALF. In separate reaction tubes, L-NIL was added to macrophages infected with PAO1 pre-opsonized with immune serum in order to block nitric oxide production in macrophages. At 5 hours, immune serum and immune BALF demonstrated superior killing compared to control BALF and untreated bacteria. (FIG. 10) The 1000-fold dilution of the immune serum abolished killing, suggesting a potential role for anti-CGL IgA as a mediator of killing. Killing was also abrogated when L-NIL was added to macrophages, suggesting that nitric oxide production is necessary for macrophage-mediated killing, independent of opsonin. On the whole, opsonization of these two heterologous GNB with a single representative sample of immune serum and BALF seems to mediate killing activity with PM, but this was not observed with this particular assay when using AM.

Example 10

Protection Against Respiratory Tularemia with dLPS-J5/OMP Vaccine with CpG ODN

BALB/c mice were immunized with the vaccine at 1 mcg/mouse intranasally at days 0, 14 and 28. One group of mice received the vaccine+CpG at 25 mcg/mouse (&/group), another received vaccine alone (i.e. no CpG) (n=7), a third group received CpG alone (n=3) and a fourth group received saline (n=3). Twenty-eight days after the final immunization, all mice were administered 8-10,000 CFUs of the LVS strain of *F. tularensis* and followed for survival.

No difference was observed between the CpG alone and saline groups. Hence, they were grouped together as "control". Similarly, since there was no difference between vaccine alone and vaccine+CpG, they were grouped together as "vaccinated". Analysis of survival by the Kaplan Meier method (FIG. 11) showed a difference in survival between control and vaccinated that was significant at a p value of 0.0012. Thus, the data presented herein suggests that immunization with the endotoxin vaccine may protect the subjects from lethal inhalation tularemia. Based on the results disclosed herein, the mechanism of action of the vaccine in protecting the immunized mice from developing the infection was examined.

Figure 12:
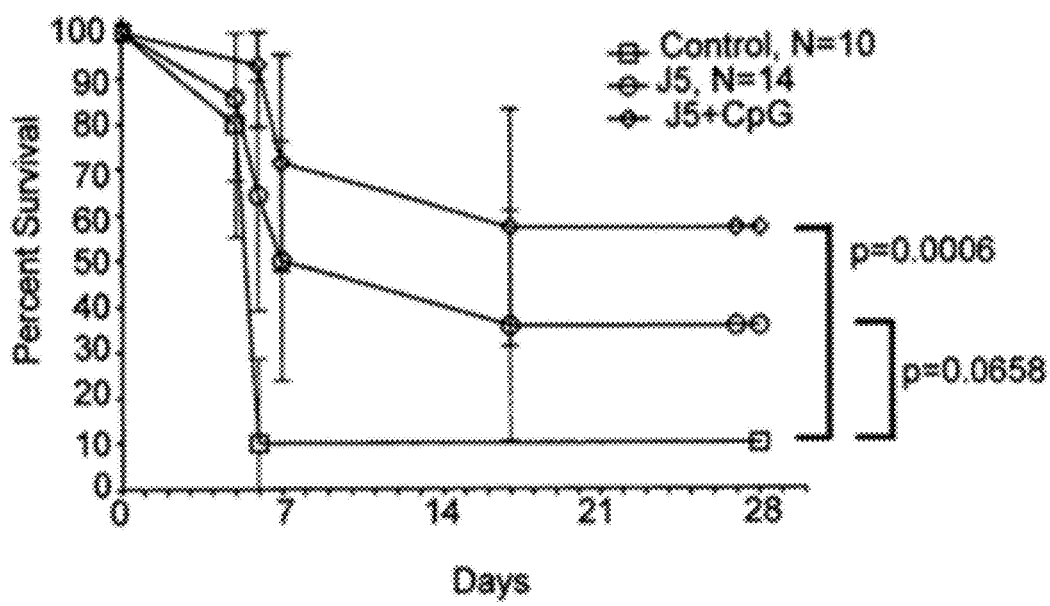
FIG. 12 shows that intratracheal (i.t) challenge with LVS (live attenuated FT vaccine) 4 weeks after the last immunization of BALB/c mice with vaccine+CpG conferred protection. Data represents two separate experiments.
Figure 13A:
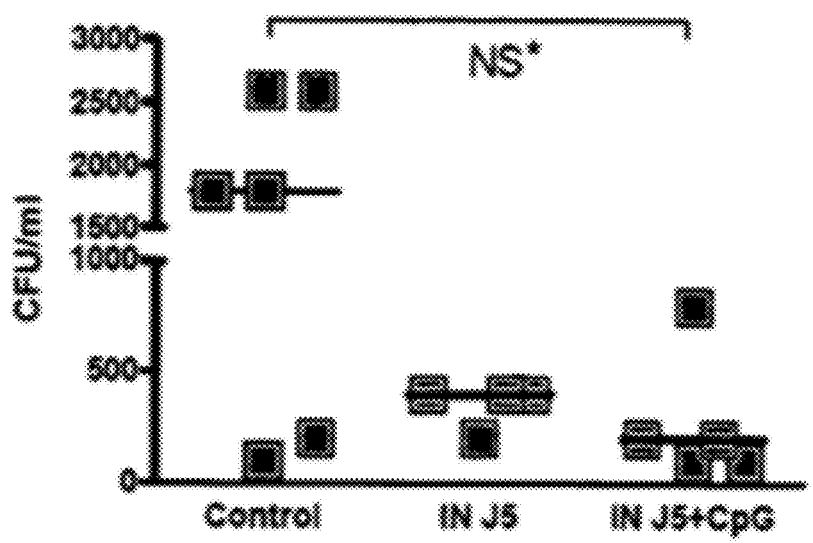
FIGS. 13A-13E show that protection against lethal LVS i.t challenge correlated with reduced levels of bacteria in blood, lung and liver at 96 hours.
Figure 13B:
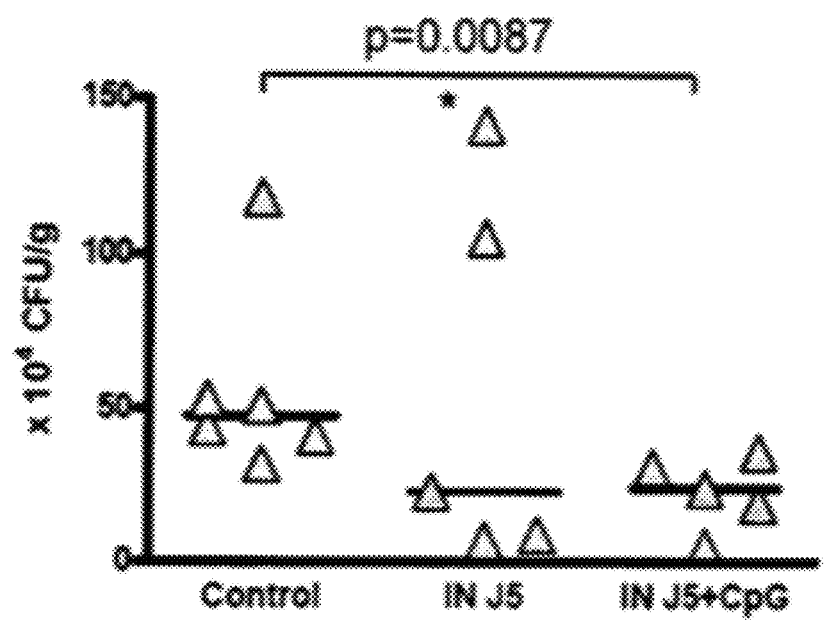
Figure 13C:
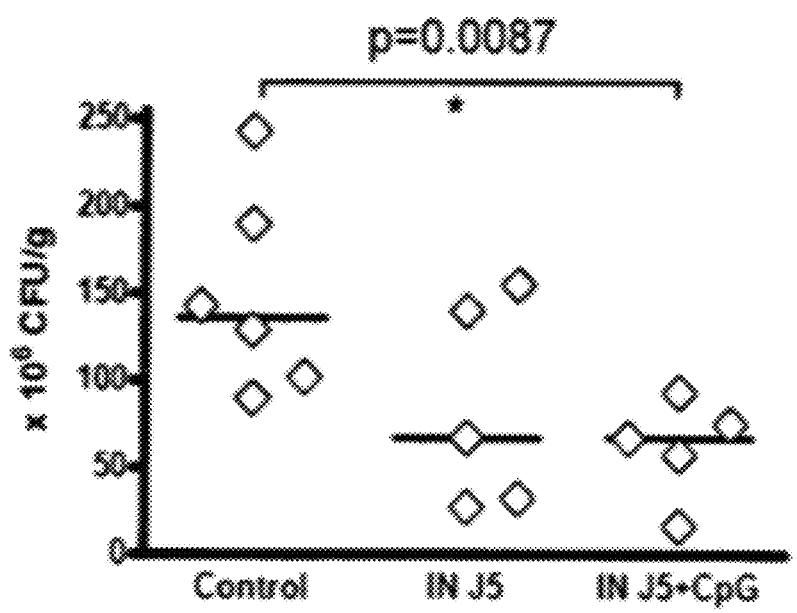
Figure 13D:
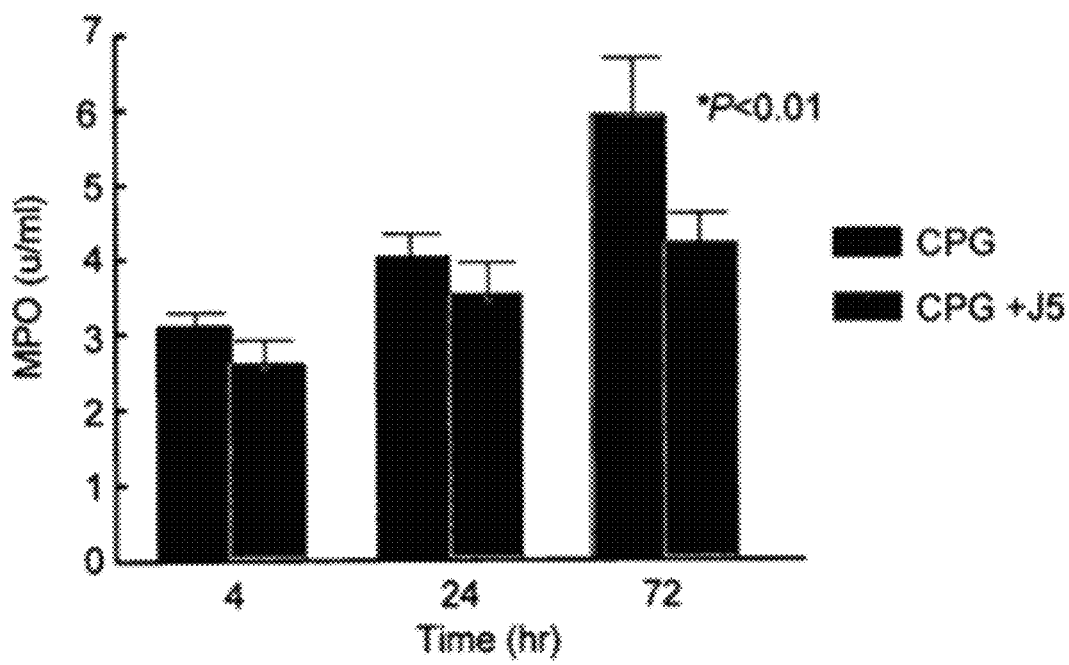
Figure 13E:
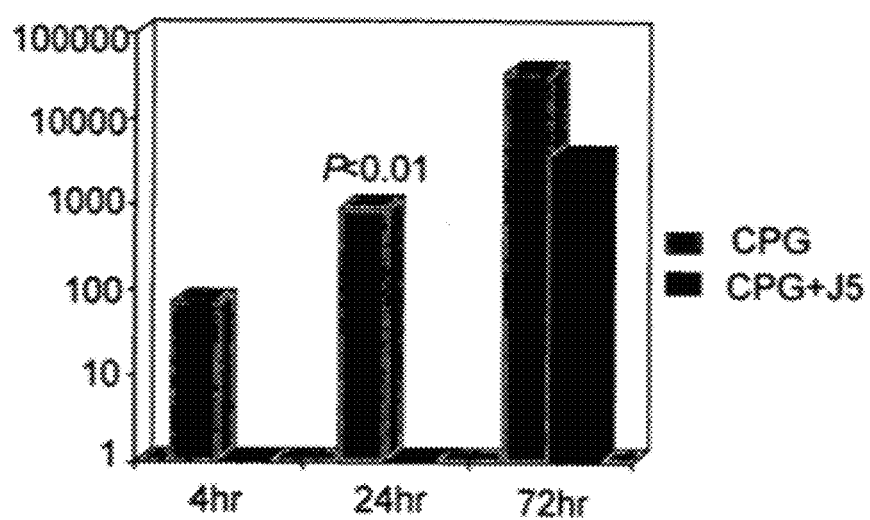

Immunization of BALB/c mice i.n. with vaccine and CPG or CPG alone at time 0, day 14 and day 28 induced IgG and IgA antibodies against the J5 CGL in both serum and BAL fluid. Intratracheal challenge with LVS 4 weeks after the last immunization with vaccine+CPG revealed 22/36 mice survived compared to ⅛ mice immunized with CPG and ⅒ PBS controls (p<0.0001) (FIG. 12). Mice immunized with vaccine+CPG had fewer viable FT colonies in lung homogenates (p<0.0087), and less extra-pulmonary dissemination to liver and spleen than CPG controls (p<0.01) (FIGS. 13A-13E). Conceivably, the lower levels of cytokine (IL-12, TNFa, IFNg and IL-4) mRNA in lung and liver homogenates were due to fewer bacteria (Table 4). Immunized animals also had fewer neutrophils recruited to the lungs (FIG. 13D). Based on these data, BALB/c mice were immunized i.n. with either CPG alone or CPG+vaccine using the same immunization schedule. Four weeks later, mice were challenged i.t. with ~10 cfu of SchuS4. Whereas 4/18 mice receiving CPG alone survived, 13 of 20 mice immunized with vaccine+CPG survived (p<0.01). The present invention contemplates determining the ability of post-immunization BAL and sera to kill FT in vitro and identifying the epitope to which the anti-CGL antibody binds. However, based on the data presented herein it is concluded that i.n. immunization against FT with this vaccine and CPG merits further investigation. Additionally, the present invention contemplates assessing the efficacy of the vaccine disclosed herein in protection against plague. Furthermore, the vaccine efficacy will be evaluated in a second animal model as well ("two animal" rule).

TABLE 4

Levels of pro-inflammatory cytokines (g/mcg protein) in control and vaccinated mice

| | IFN-γ Control | IFN-γ Vaccinated | IL-1α Control | IL-1α Vaccinated | IL-6 Control | IL-6 Vaccinated | KC Control | KC Vaccinated | TNF-α Control | TNF-α Vaccinated |
|---|---|---|---|---|---|---|---|---|---|---|
| Lung Day 0 | 44 | 53 | 205 | 97 | 98 | 170 | 85 | 30 | 1289 | 1041 |
| Lung Day 3 | 121 | 60 | 174 | 115 | 60 | 205 | 80 | 28 | 632 | 1206 |
| Liver Day 0 | 33 | 39 | 1023 | 1120 | 598 | 1011 | 861 | 589 | 2137 | 6287 |
| Liver Day 3 | 186 | 35 | 975 | 257 | 367 | 163 | 577 | 118 | 1067 | 1027 |

Cytokines were analyzed from control and vaccinated mice. Samples were pooled and were analyzed by BioPlex on day of first challenge (Day 0) and 3 days later (Day 3).

Example 11

Study in Healthy Human Subjects

Subject Groups and Design

This study was designed as a randomized, partial blind, placebo-controlled, Phase I study in healthy adults, 18-50 years old to evaluate the safety, reactogenicity and immunogenicity of J5dLPS-GBOMP vaccine with or without CPG 7909, an oligo deoxynucleotide based adjuvant. Subjects were randomized to one of four groups: (1) J5dLPS/GBOMP vaccine alone (10 μg); or (2) J5dLPS/GBOMP vaccine (10 μg) with CPG 7909 adjuvant (250 μg); or (3) J5dLPS/GBOMP vaccine (10 μg) with CPG 7909 adjuvant (500 μg); or (4) placebo (normal saline). Each subject was to receive 3 separate intramuscular (IM) vaccinations on Day 0, Day 29, and Day 59 (Table 5).

Initially 2 subjects in each of the following groups received either unadjuvanted vaccine, vaccine adjuvanted with 250 μg CPG 7909 or placebo. Upon favorable SMC review of safety and clinical laboratory data obtained through day 7 after the second immunization and 30 days after the first immunization, the remaining 6 subjects in the unadjuvanted vaccine and 6 in the 250 μg-adjuvanted vaccine groups were immunized along with 2 subjects in the 500 μg-adjuvanted vaccine group. Following favorable review obtained through day 7 after the second immunization and 30 days after the first immunization of the 500 μg-adjuvanted vaccine group, the remaining 6 subjects in this cohort would have been immunized along with the remaining two subjects in the placebo group.

Subjects were followed for safety and reactogenicity. Subjects were observed in the clinic for at least 60 minutes after each vaccination by blinded study personnel for any adverse signs or symptoms. Subjects had to maintain a memory aid for Days 0-7 on which they were expected to record their daily oral temperature and any systemic and local reactogenicity that occurred within the week following each vaccination. Subjects had to return to the clinic for 2 consecutive days after each vaccination to have their blood drawn for CBC with differential, ANC and ALC, their arm checked for any redness or swelling, and for an EKG. In the event of a grade 3 neutropenia or lymphopenia identified on any of the safety laboratory tests, subjects take their temperature each evening until normalization of CBC. Follow up CBC are performed every 2-3 days thereafter until normalization, and the subjects are called each day to establish whether there were any problems. In the event of fever, subjects had to return to the clinic for evaluation by the PI or designee who would then decide if a further medical workup was indicated. Abnormal values for other parameters in the CBC were evaluated for clinical significance by the PI. All subjects return to the clinic 7 to 10 days after each vaccination for review of the memory aid, assessment of AEs, concomitant medications and blood draws (safety labs). Following the third vaccination, subjects returned for follow-up clinical visits for the assessment of adverse events on days 120, 180, and 365. In addition, a safety follow-up call occurred on Day 90, Day 150 and Day 239.

Serum samples were obtained at various time-points pre and post vaccination (Days 0, 14, 36, 66, 120, 180 and 365) for the assessment of IgG and IgM antibody responses to relevant antigens (J5 LPS, OMP) and for functional opsonophagocytic activity against various gram negative organisms. Since adjuvants rarely may induce an autoimmune response, an immunology safety panel consisting of anti-nuclear antibody (ANA) and anti-double stranded DNA was obtained at Days 0, 14, 36, 66, 120, 180 and 365.

TABLE 5

Study Design

| Group | No. of Subjects | Vaccine/Placebo | Adjuvant Dose | Vaccination Days | | |
|---|---|---|---|---|---|---|
| A | 8 | 10 μg J5dLPS-GBOMP vaccine | N/A | 0 | 29 ± 2 | 59 ± 2 |
| B | 8 | 10 μg J5dLPS-GBOMP vaccine | 250 μg CPG 7909 | x | x | x |
| C | 8 | 10 μg J5dLPS-GBOMP vaccine | 500 μg CPG 7909 | x | x | x |
| D | 4 | Normal saline (placebo) | N/A | x | x | x |

Endpoints

Mean fold-increase in anti-J5 dLPS IgG and IgM levels in the serum of subjects and percent of subjects having >4-fold IgG and IgM antibody titer response over baseline at Days 14, 36, 66, 120, 180 and 365. Time to seroconversion was analyzed by comparing the number of subjects with >4-fold increases over baseline in antibody responses in each group at each time point.

Summary of Safety Results

The vaccine was well-tolerated and safe, even when given with 250 or 500 mcg CPG. There were no severe adverse reactions (or deaths) in any study group. There were moderate systemic events, primarily fatigue and malaise, primarily after the first immunization. Local reactions were also of moderate severity. There was no evidence of vaccine-related increase in anti-nuclear antibodies or unsolicited adverse effects of special interest. One subject had an increase in TSH levels probably unrelated to immunization (first elevation occurred 127 days after the last immunization).

Summary of Immunogenicity Results

The J5dLPS/OMP vaccine alone was poorly immunogenic in this study. Addition of 250 mcg CPG 7909 increased and accelerated the IgG and IgM response to J5 LPS and these responses persisted for 180 days and beyond without further vaccination. Although only two subjects received the vaccine and CPG 500 mcg, there was a suggestion that the higher dose CPG resulted in a more robust antibody response than with the CPG 250 mcg.

Summary and Conclusions

The J5dLPS/OMP vaccine was safe and well-tolerated and the addition of CPG did not alter that conclusion. The combination of vaccine with CPG increased the number of subjects with a four-fold or greater antibody response to the vaccine and this response was evident even after the second of three planned doses.

Results of Vaccination

Figure 14:
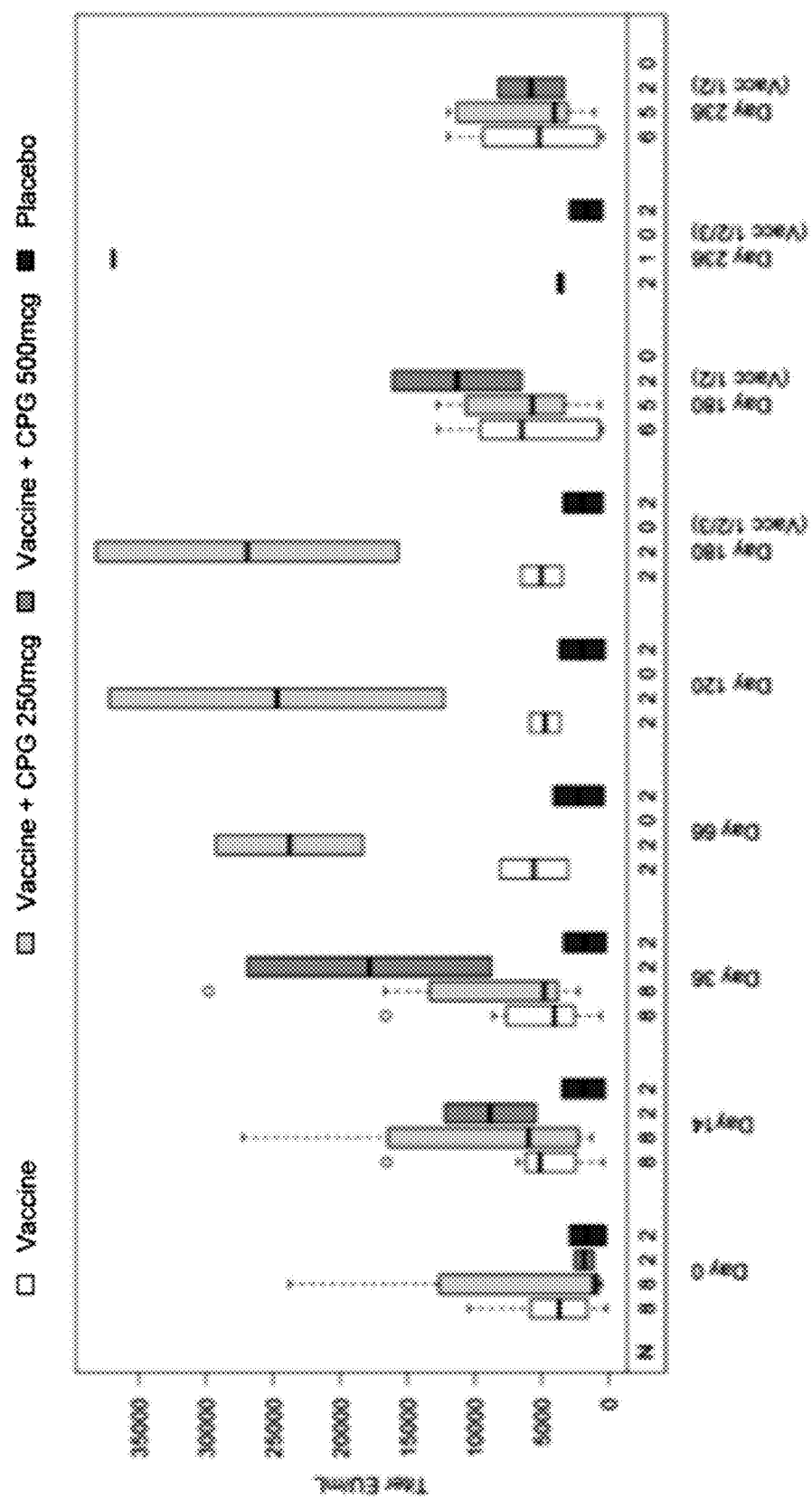
FIG. 14 shows the geometric mean result for IgG titer response to the J5 antigen for a 1:1000 dilution.

Two of eight subjects in each of the vaccine alone and vaccine+CPG 250 mcg groups received all 3 vaccinations. Only two subjects in the placebo group were vaccinated, both received all 3 vaccinations. The two subjects in the vaccine+CPG 500 mcg group received only the first two vaccinations. There is evidence that the IgG antibody responses in the vaccine+CPG groups were higher than those in the vaccine alone group (FIG. 14). While the vaccine alone group had higher antibody levels than the placebo group, only 1 of 8 had a four-fold increase over baseline after the primary vaccination series (i.e. 3 vaccinations). In contrast, the vaccine+CPG 250 mcg group had both a higher geometric mean-fold increase (gMFI) over baseline than did the vaccine alone group and a greater percentage of subjects in the CPG group had a >4-fold increase in antibody level over baseline. Two subjects received vaccine+CPG 500, both subjects achieved a >4-fold response after only the second immunization and the gMFI was 3 times that of the 250 mcg group. Of note, the elevated IgG levels persisted through day 180. When the number of responders (>4-fold increase over baseline) after the second immunization was compared, addition of CPG (either dose) produced a higher proportion of responders (⅛ vaccine alone vs 5/10 vaccine+CPG).

Figure 15:
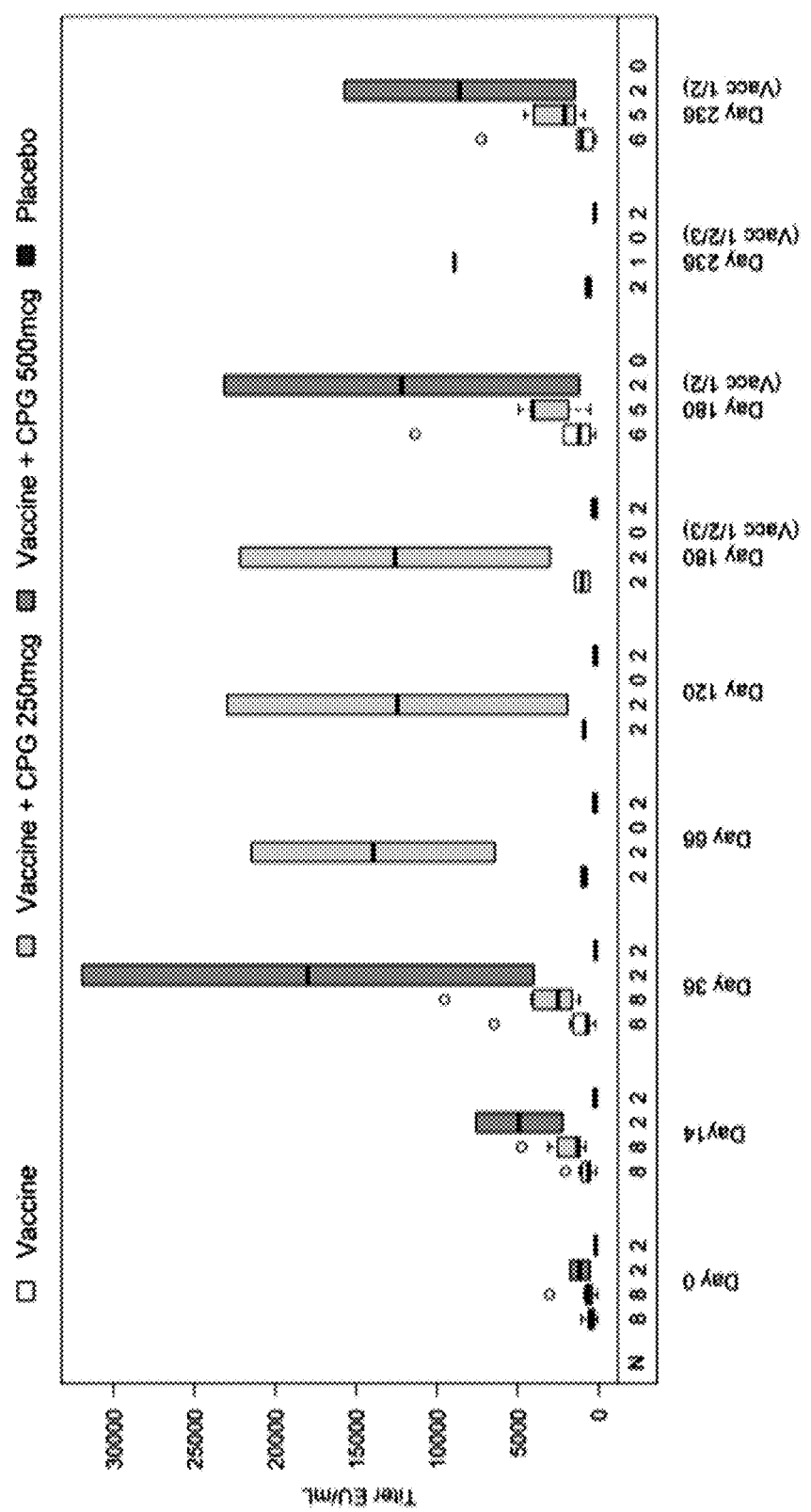
FIG. 15 shows the Geometric Mean Result for IgM titer Response to J5 Antigen by Visit and Group for 1:1000 Dilution.

After the first vaccination there was a robust IgM response in the two CPG groups, with over a 4-fold gMFI increase in the two subjects in the 500 mcg CPG group and nearly a three-fold increase in the CPG 250 mcg group (FIG. 15). Following the second vaccination the IgM level increased further in the CPG 500 mcg group (gMFI 11.54) and in the CPG 250 mcg group (gMFI 4.82), while the vaccine only group had a gMFI of 2.43 which was essentially unchanged after the third vaccination. The proportion of responders in the vaccine alone group (25%) is lower than the observed proportion in the two combined CPG groups (60%). Table 6 summarizes the results for the ELISA titer responses to J5 antigen after the second immunization on day 36. Vaccine response is defined as a 4-fold or greater increase over baseline level and gMFI is the geometric mean fold increase in antibody titer over baseline.

TABLE 6

ELISA titer responses to J5 antigen after second immunization

|  | Vaccine + CPG 500 mcg | Placebo | Vaccine + CPG 500 mcg | Placebo |
|---|---|---|---|---|
| IgM Response |  |  |  |  |
| >4-fold | 2/2 | 0/2 | 4/8 | 2/4 |
| gMFI | 11.54 | 1.01 | 4.82 | 2.4 |
| IgG Response |  |  |  |  |
| >4-fold | 2/2 | 0/2 | 3/8 | 1/8 |
| gMFI | 9.03 | 1.06 | 2.75 | 1.6 |

Example 12

Non-Alum Adjuvants in a Murine Model

Figure 16:
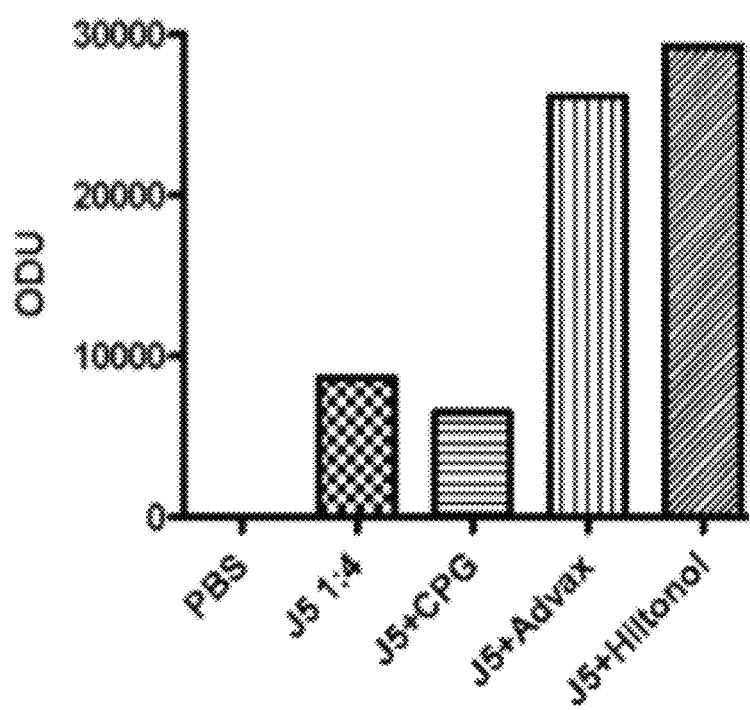
FIG. 16 shows that the HILTONOL and ADVAX adjuvants enhanced the antibody response to the J5dLPS/OMP vaccine. Antibody response expressed as optical density units ODU.

It has been shown previously that adding alum to the vaccine actually impaired the immune response. Thus, CD-1 mice were immunized with the J5dLPS/OMP vaccine either alone or with CPG, ADVAX or HILTONOL and the antibody response was measured after the last of 3 vaccinations. CD-1 mice were immunized at Days 0, 14 and 28 with 10 mcg (J5 1:4 dilution of stock), J5dLPS/OMP vaccine alone, or with CpG (25 ug), ADVAX or HILTONAL. The data show that the vaccine alone induced antibodies (by ELISA) compared to placebo (normal saline) mice, but that addition of HILTONOL and ADVAX improved the antibody response considerably (FIG. 16). This demonstrates that other adjuvants beyond CPG can boost the immune response.

The following references were cited herein:
1. Cross A. S. et al., *Vaccine* 2003; 21:4576-4588.
2. Bhattacharjee A. K. et al., *J Infect Dis* 1996; 173:1157-1163.
3. Bhattacharjee A. K. et al., *J Infect Dis* 1994; 170:622-629.
4. Cross A. S. et al. *J Infect Dis* 2001; 183:1079-1086.
5. Bauer S. *Proc Natl Acad Sci USA* 2001; 98:9247-9242.
6. Hemmi H. et al. *Nature* 2000; 408:740-744.
7. McCluskie M. J. et al., *Vaccine* 2001; 19: 2657-2660.
8. Weighardt H. et al, *J Immunol* 2000; 165:4537-4543.
9. Wild J. S. and Sur S. *Allergy* 2001; 56(5):365-376.
10. Rothenfusser S. et al., *Curr Opin Mol Ther* 2003; 5(2):98-106.
11. Halperin S. et al., *Vaccine* 2003; 21:2461-2467.
12. Cooper C. L. et al., *Vaccine* 2004; 13:136-143.
13. Von Hunolstein C. et al., *Int Immunol* 2000; 12(3):295-303.
14. Chu R. S. et al., *Infect Immun* 2000; 68(3):1450-1456.
15. Cross A. S. et al., *Vaccine* 2004; 22:812-817.
16. Cross A. S. et al., *Infect Immun* 1993; 61(7):2741-7.
17. Joseph A. et al., *Vaccine* 2002; 20:3342-3354.
18. Klinman D. M. *Expert Rev Vaccines* 2003; 2(2):305-315.
19. Gao J. J. et al., *Immunol* 2001; 166:6855-6860.
20. Malanchere-Bres E. et al., *J Virol* 2001; 75(14):6482-6491.
21. Khan A. Q. et al. *J Immunol* 2004; 172(1):532-539.
22. Opal S. M. et al., *J Infect Dis* 2005; 192(12):2074-80.
23. Hirano et al., *FEMS Immunol Med Microbiol* 2003; 35(1): 1-10.

24. Jiao et al., *Infect Immunol* 2002; 70(11): 5982-9.
25. Bhattacharjee A. K. et al., *Infect Immun* 2002; 70(7): 3324-9.
26. Van d et al., *Infect Immun* 1996; 64(12): 5263-8.
27. Orr et al., *Infect Immun* 1993; 61(6): 2390-5.
28. DiGiandomenico et al., *Proc Natl Acad Sci USA* 2007; 104(11): 4624-9.
29. Brandtzaeg P., *Vaccine* 2007; 25(30): 5467-84.
30. Snoeck et al., *Vet Res* 2006; 37(3):455-67.
31. Renegar et al., *J Immunol* 2004; 173(3): 1978-86.
32. McCluskie and Davis., *Vaccine* 1999; 18(3-4): 231-7.
33. Wongratanacheewin et al., *Infect Immun* 2004; 72(8): 4494-502.
34. Elkins et al., *J Immunol* 1999; 162(4): 2291-8.
35. Klinman D. M. *Infect Immun* 1999; 67(11):5658-63.
36. Deng et al., *J Immunol* 2004; 173(8):5148-55.
37. Nichani et al., *Vet Immunol Immunopathol* 2007; 115(3-4):357-68.
38. LaForce et al., *J Infect Dis* 1980; 142(3):421-31.
39. Robbins et al., *Clin Infect Dis* 1992; 15(2):346-361.
40. Martin and Frevert, *Proc Am Thorac Soc* 2005, 2(5): 403-411.
41. Opal S. M. et al., *Shock* 2001; 15(4):285-290.
42. Trautmann et al., *Infect Immun* 1994; 62(4): 1282-8.
43. Kang et al., *Infect Immunol* 2005; 73(11): 7495-501.
44. Lu et al., *J Immunol* 2006; 176(7): 3890-4.
45. Opal S. M. et al., *J Infect Dis* 2005; 192(12):2074-80.

What is claimed is:

1. An immunogenic composition, consisting of:
   a detoxified *E. coli* J5 core lipopolysaccharide of the Rc chemotype, non-covalently complexed with group B meningococcal outer membrane protein; and
   CpG 7909.

2. A method of actively immunizing an individual against infection by a heterologous Gram negative bacterium comprising administering to the individual an immunologically effective amount of the immunogenic composition of claim 1.

3. The method of claim 2, wherein the immunogenic composition is administered subcutaneously, intramuscularly, or intranasally.

4. The method of claim 2, wherein the detoxified *E. coli* J5 core lipopolysaccharide non-covalently complexed with the group B meningococcal outer membrane protein is present in the immunogenic composition in a concentration of 5 to 50 micrograms and the CpG 7909 is present in the immunogenic composition in a concentration of 250 to 500 micrograms.

5. The method of claim 2, wherein the immunogenic composition elicits anti-J5 core lipopolysaccharide antibodies in the individual that bind to the heterologous Gram negative bacterium.

* * * * *